US008278115B2

(12) United States Patent
Coon et al.

(10) Patent No.: US 8,278,115 B2
(45) Date of Patent: Oct. 2, 2012

(54) METHODS FOR PROCESSING TANDEM MASS SPECTRAL DATA FOR PROTEIN SEQUENCE ANALYSIS

(75) Inventors: Joshua J. Coon, Middleton, WI (US); Gheorghe Craciun, Madison, WI (US); Shane Lauson Hubler, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 805 days.

(21) Appl. No.: 12/323,766

(22) Filed: Nov. 26, 2008

(65) Prior Publication Data
US 2009/0173878 A1  Jul. 9, 2009

Related U.S. Application Data

(60) Provisional application No. 60/991,398, filed on Nov. 30, 2007.

(51) Int. Cl.
G01N 24/00 (2006.01)
(52) U.S. Cl. .............................. 436/173; 436/86; 436/89
(58) Field of Classification Search .................. None
See application file for complete search history.

(56) References Cited

U.S. PATENT DOCUMENTS

| | | | |
|---|---|---|---|
| 6,500,650 B1 | 12/2002 | Stanton, Jr. et al. | |
| 6,566,059 B1 | 5/2003 | Stanton, Jr. et al. | |
| 6,582,923 B2 | 6/2003 | Stanton, Jr. et al. | |
| 6,610,492 B1 | 8/2003 | Stanton, Jr. et al. | |
| 6,777,188 B2 | 8/2004 | Stanton, Jr. et al. | |
| 6,825,009 B2 | 11/2004 | Stanton, Jr. et al. | |
| 6,838,663 B2 | 1/2005 | Coon et al. | |
| 6,878,933 B1 | 4/2005 | Coon | |
| 7,534,622 B2 | 5/2009 | Hunt et al. | |
| 2005/0009053 A1 | 1/2005 | Boecker et al. | |
| 2005/0074816 A1 | 4/2005 | Duncan et al. | |
| 2006/0243900 A1 | 11/2006 | Overney et al. | |

FOREIGN PATENT DOCUMENTS

| | | |
|---|---|---|
| WO | WO 2005057208 A1 * | 6/2005 |
| WO | WO 2005/090978 | 9/2005 |
| WO | WO 2006/042187 | 4/2006 |
| WO | WO 2007/015690 | 2/2007 |
| WO | WO 2009/073505 | 6/2009 |

OTHER PUBLICATIONS

Busch "Chemical Noise, Part IV: Reduction of Noise through Informatics" Spectroscopy, Feb. 2004, v. 19, No. 2, pp. 44-52.*

(Continued)

Primary Examiner — Yelena G Gakh
(74) Attorney, Agent, or Firm — Greenlee Sullivan P.C.

(57) ABSTRACT

Various mass spectroscopy-based methods are provided to improve protein sequencing by detecting z-type product ions generated from the protein. A polypeptide is introduced to a mass spectrometer, and in particular c- and z-type product ions that are generated by selectively fragmenting the polypeptide. The z-type product ions are distinguished from the c-type product ions and the mass-to-charge ratio of at least a portion of the z-type product ions are determined. From the mass of the z-type product ions, a putative chemical composition is identified for at least a portion of the z-type product ions, c-type product ions, or both, which is used to determine polypeptide compositions. Further provided are various methods for reducing spectral noise, instrument calibration and database searching and verification.

20 Claims, 20 Drawing Sheets

18A

18B

OTHER PUBLICATIONS

Eng, et al. (1994) "An Approach to Correlate Tandem Mass Spectral Data of Peptides with Amino Acid Sequences in a Protein Database," *J. Am. Soc. Mass Spectrom.*, 5:976-989.

Geer et al. (2004) "Open Mass Spectrometry Search Algorithm," *Journal of Proteome Research*, 3:958-964.

Chi et al. (Feb. 13, 2007) "Analysis of Phosphorylation Sites on Proteins from *Saccharomyces cerecisiae* by Electron Transfer Dissociation Mass Spectrometry," *Proc. Nat. Acad. Sci. USA* 104(7):2193-2198.

Coon et al. (2005) "Electron Transfer Dissociation of Peptide Anions," *J. Am. Soc. Mass Spectrom.* 16:880-882.

Coon et al. (Web Release Jun. 19, 2004) "Anion Dependence in the Partitioning between Proton and Electron Transfer During Ion/Ion Reactions," *Int. J. Mass Spectrom.* 236:33-42.

Coon et al. (2005) "Tandem Mass Spectrometry for Peptide Sequence Analysis," *Biotechniques* 38(4):519-523.

Coon et al. (Jul. 5, 2005) "Protein Identification Using Sequential Ion/Ion Reactions and Tandem Mass Spectrometry," *Proc. Nat. Acad. Sci. USA* 102(27):9463-9468.

Coon et al. (Web Release Sep. 14, 2002) "Laser Desorption-Atmospheric Pressure Chemical Ionization Mass Spectrometry for the Analysis of Peptides from Aqueous Solutions," *Anal. Chem.* 74(21):5600-5605.

Coon et al. (2002) "Atmospheric Pressure Laser Desorption/Chemical Ionization Mass Spectrometry: A New Ionization Method Based on Existing Themes," *Rapid Commun. Mass Spec.* 16:681-685.

Dodds (Web Release Apr. 19, 2006) "Enhanced Peptide Mass Fingerprinting Through High Mass Accuracy: Exclusion of Non-Peptide Signals Based on Residual Mass," *J. Proteome Res.* 5:1195-1203.

Frank et al. (Web Release Nov. 18, 2006) "De Novo peptide Sequencing and Identification with Precision Mass Spectrometry," *J. Proteome Res.* 6:114-123.

Good et al. (2006) "Advancing Proteomics with Ion/Ion Chemistry," *Biotechniques* 40(6):783-789.

Gross, M.L. (Jun. 1994) "Accurate Masses for Structure Confirmation," *J. Am. Soc. Mass Spectrom.*5:57.

He et al. (Web Release Dec. 10, 2003) "Theoretical and Experimental Prospects for Protein Identification Based Solely on Accurate Mass Measurement," *J. Prot. Res.* 3:61-67.

Hubler et al. (2008) "Valene Parity Renders z•-Type Ione Chemically Distinct," *J. Am. Chem. Soc.* 130(20):6388-6394.

Hunt et al. (Sep. 1986) "Protein Sequencing by Tandem Mass Spectrometry," *Proc. Nat. Acad. Sci. USA* 83:6233-6237.

International Search Report and Written Opinion, Corresponding to International Application No. PCT/US2008/084822, Mailed Jul. 14, 2009.

Liu et al. (Web release Nov. 13, 2007) "On the Value of Knowing z• Ion for What it is," *J. Proteome Res.* 7(1):130-137.

Malek et al. "Electron Capture Dissociation on the LTQ? ? Preserving Post-Translational Modifications During Peptide Fragmentation," http://www.thermo.com/com/cda/resources/resources_detail/1,,111653,00.html Viewed on Oct. 22, 2007.

McAlister et al. (Web Release Apr. 19, 2007) "Implementation of Electron Transfer Dissociation on a Hybrid Linear Ion Trap-Orbitrap Mass Spectrometer," *Anal. Chem.* 79(10):3525-3534.

Nielsen et al. (2005) "Improving Protein Identification Using Complementary Fragmentation Techniques in Fourier Transform Mass Spectrometry," *Mol. Cell. Proteom.* 4:835-845.

Roepstorff et al. (1984) "Proposal for a Common Nomenclature for Sequence Ions in Mass Spectra of Peptides," *Biomed. Mass Spectrom.* 11(11):601.

Savitski et al. (Web Release Oct. 26, 2005) "Proteomics-Grade de Novo Sequencing Approach," *J. Proteome Res*.4:2348-2354.

Spengler, B. (2007) "Accurate Mass as a Bioinformatic Parameter in Data-to-Knowledge Conversion: Fourier Transform Ion Cyclotron Resonance Mass Spectrometry for Peptide de Novo Sequencing," *Eur. J. Mass Spectrom.* 13:83-87.

Swaney et al. (Web Release Dec. 8, 2006) "A Supplemental Activation Method for High Efficiency Electron Transfer Dissociation of Doubly Protonated Peptide Precursors," *Anal. Chem.* 79(2):477-485.

Syka et al. (Jun. 29, 2004) "Protein Sequence Analysis Using Electron Transfer Dissociation Mass Spectrometry," *Proc. Nat. Acad. Sci. USA* 101(26):9528-9533.

Tsybin et al. (Web Release Sep. 17, 2007) "Ion Activation in Electron Capture Dissociation to Distinguish Between N-Terminal and C-Terminal Product Ions," *Anal. Chem.* 79(20):7596-7602.

Williams et al. (Web Release Sep. 15, 2007) "Dual Electrospray Ion Source for Electron-Transfer Dissociation on a Hybrid Linear Ion Trap-Orbitrap Mass Spectrometer," *Anal. Chem.* 79(20):7916-7919.

Zubarev et al. (Web Release Mar. 24, 1998) "Electron Capture Dissociation of Multiply Charged Protein Cations. A Nonergodic Process," *J. Am. Chem. Soc.* 120(13):3265-3266.

Zubarev et al. (Nov. 15, 1996) "Accuracy Requirements for Peptide Characterization by Monoisotopic Molecular Mass Measurements," *Anal. Chem.* 68:4060-4063.

\* cited by examiner

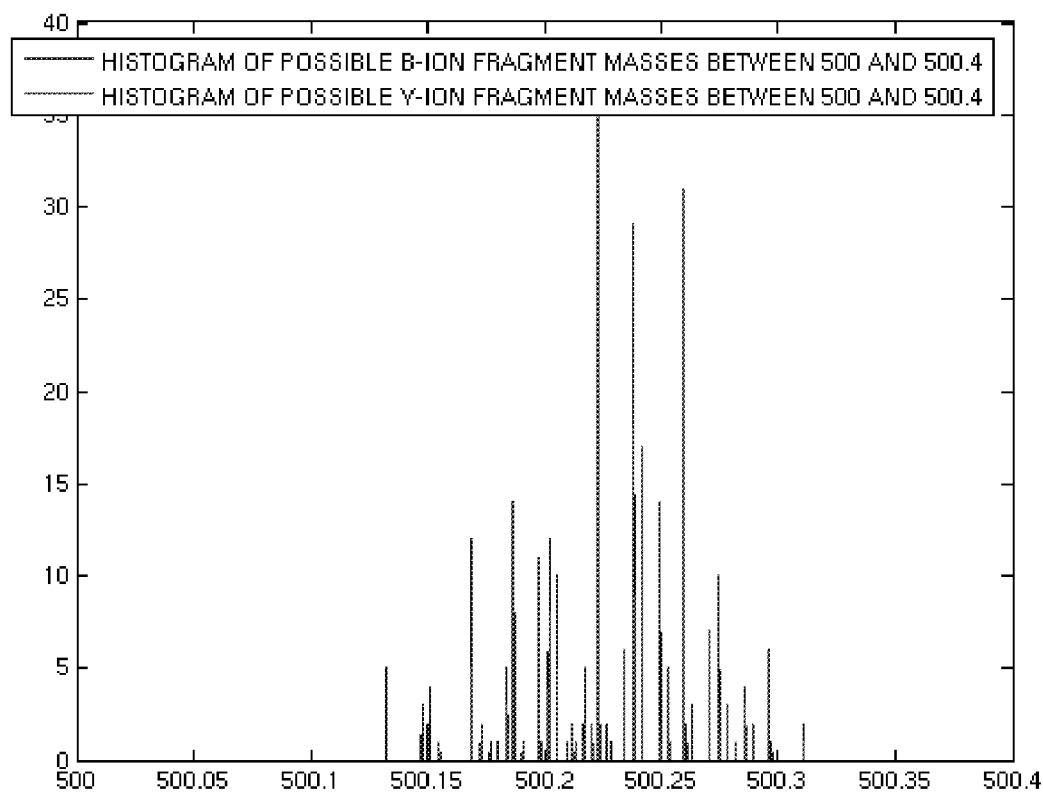
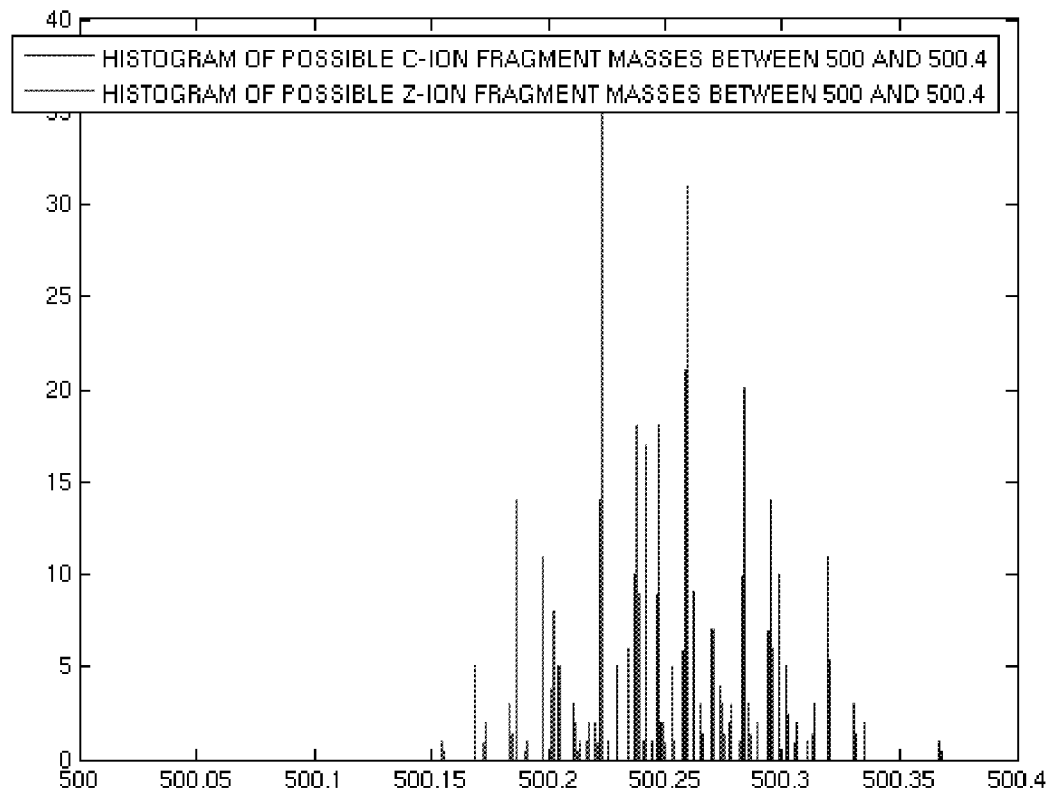
Figure 9

Ion ID: Output File

TotalMass: 844.5184
Peak: 159.100183 17221.2 1
  Ion: z-ion 2003006013 159.100228809
Peak: 229.129629 3620.4 1
  Ion: c-ion 3004009017 229.129516833 6
Peak: 290.140662 2785.4 1
  Ion: z-ion 1003004011022 290.140712995171
Peak: 344.24043 23638.3 1
  Ion: c-ion 3007014030 344.240464265371
Peak: 389.208716 3829.3 1
  Ion: z-ion 1004005016021
Peak: 457.324192 5001.3 1
  Ion: c-ion 4008020041 457.324528242831
Peak: 459.238147 2970.1 1
  Ion: c-ion 1005006019035 459.238415661191
Peak: 501.285604 1771 1
  Ion: c-ion 1005008022041 501.285385857 91
Peak: 502.292897 21621.2 1
  Ion: c-ion 1005008022042 502.293190885891
... 75 1
  Ion: c-ion 1005007022044 518.311914954891
Peak: 556.392582 8523.6 1
  Ion: c-ion 5009025050 556.392942156091
Peak: 603.339492 2916.1 1
  Ion: c-ion 1006010024047 603.339526685151
Peak: 616.372921 2094.8 1
  Ion: z-ion 1006008027052 616.372503836051
Peak: 658.394437 2988.5 2
  Ion: z-ion 1006100028054 658.394301909851
  Ion: c-ion 1007007030056 658.395644579211
Peak: 687.433305 31225.2 1
  Ion: c-ion 1006010030059 687.433427070 35
Peak: 688.430243 14661.3 1
  Ion: c-ion 9009030058 688.435200891131
Peak: 689.441195 2122.2 1
  Ion: c-ion 8012028057 689.441683253871
Peak: 715.415097 1247.6 4
  Ion: z-ion 8008035055 715.413737 17047
  Ion: c-ion 1006014028055 715.414422961151
  Ion: z-ion 9005037057 715.415079839831
  Ion: c-ion 1007011030057 715.415765630511

- Total Mass – From .dta File
- Peak Mass-to-Charge – From .dta File
- Peak Intensity – From .dta File
- Number of possible fragments explained by peak (at 4 ppm)
- Fragment Mass – Calculated
- Fragment Chemical Composition Number (S O N C H)
- Example: $S_1 O_6 N_{14} C_{28} H_{55}$
- Fragment type
  - Can be "MANY" when more than five fragment compositions are possible
  - Can be "Out-Of-Bounds" when mass greater than 1750 Daltons File: 052007_yeast60min_FTFT_Recal.1010.1010.3.dta

Figure 10

| | Matched | | Score | | | | Relate 1st to 2nd | | |
|---|---|---|---|---|---|---|---|---|---|
| | | | OMSSA | | CnZion | | | | |
| | Best OMSSA | An OMSSA | Best | Matched | Best | 2nd Best | Ratio | Difference | Number of Best Answer |
| 1002.3.dta | TRUE | TRUE | 1.28E-05 | 1.28E-05 | 10 | 5 | 2.00 | 5 | 1 |
| 1008.4.dta | TRUE | TRUE | 4.95E-03 | 4.95E-03 | 3 | 2 | 1.50 | 1 | 1 |
| 1010.3.dta | TRUE | TRUE | 3.92E-07 | 3.92E-07 | 9 | 4 | 2.25 | 5 | 1 |
| 1012.4.dta | TRUE | TRUE | 6.32E-01 | 6.32E-01 | 2 | 2 | 1.00 | 0 | 3 |
| 1017.5.dta | FALSE | FALSE | 1.39E-06 | 1.39E-06 | 2 | 2 | 1.00 | 0 | 11 |
| 1029.4.dta | TRUE | TRUE | 4.87E-10 | 4.87E-10 | 7 | 3 | 2.33 | 4 | 1 |
| 1030.3.dta | TRUE | TRUE | 3.64E-05 | 3.64E-05 | 5 | 3 | 1.67 | 2 | 1 |
| 1034.2.dta | TRUE | TRUE | 9.33E-04 | 9.33E-04 | 8 | 3 | 2.67 | 5 | 3 |
| 1036.4.dta | TRUE | TRUE | 8.02E-12 | 8.02E-12 | 7 | 3 | 2.33 | 4 | 1 |
| 1040.3.dta | TRUE | TRUE | 2.34E-06 | 2.34E-06 | 11 | 6 | 1.83 | 5 | 1 |
| 1048.4.dta | TRUE | TRUE | 1.46E-04 | 1.46E-04 | 4 | 3 | 1.33 | 1 | 1 |
| 1052.4.dta | TRUE | TRUE | 2.00E-06 | 2.00E-06 | 2 | 2 | 1.00 | 0 | 83 |
| 1054.3.dta | TRUE | TRUE | 5.15E-05 | 5.15E-05 | 4 | 3 | 1.33 | 1 | 1 |
| 1060.4.dta | TRUE | TRUE | 1.23E-08 | 1.23E-08 | 2 | 2 | 1.00 | 2 | 1 |
| 1065.4.dta | TRUE | TRUE | 3.37E-02 | 3.37E-02 | 3 | 3 | 2.00 | 0 | 11 |
| 1067.3.dta | TRUE | TRUE | 7.61E-08 | 7.61E-08 | 10 | 5 | 2.00 | 5 | 1 |
| 1071.4.dta | TRUE | TRUE | 1.81E-14 | 1.81E-14 | 8 | 4 | 2.00 | 4 | 1 |
| 1074.3.dta | TRUE | TRUE | 9.08E-04 | 9.08E-04 | 4 | 3 | 1.33 | 1 | 1 |
| 1076.4.dta | TRUE | TRUE | 4.86E-09 | 4.86E-09 | 7 | 3 | 2.33 | 4 | 1 |
| 1082.3.dta | TRUE | TRUE | 2.61E-06 | 2.61E-06 | 11 | 6 | 1.83 | 5 | 1 |
| 1084.4.dta | TRUE | TRUE | 0.50433 | 0.50433 | 4 | 4 | 1.00 | 0 | 17 |
| 1086.5.dta | TRUE | TRUE | 0.00117068 | 0.00117068 | 4 | 4 | 1.00 | 0 | 2 |
| 1089.4.dta | TRUE | TRUE | 2.91E-07 | 2.91E-07 | 6 | 4 | 1.50 | 2 | 1 |
| 1096.4.dta | FALSE | TRUE | 8.62E-05 | 0.00122634 | 5 | 4 | 1.25 | 1 | 1 |
| 1109.3.dta | TRUE | TRUE | 2.76E-08 | 2.76E-08 | 10 | 5 | 2.00 | 5 | 1 |
| 1113.4.dta | TRUE | TRUE | 4.35E-09 | 4.35E-09 | 5 | 3 | 1.67 | 2 | 1 |
| 1119.4.dta | TRUE | TRUE | 3.50E-08 | 3.50E-08 | 6 | 3 | 2.00 | 3 | 1 |

Figure 17

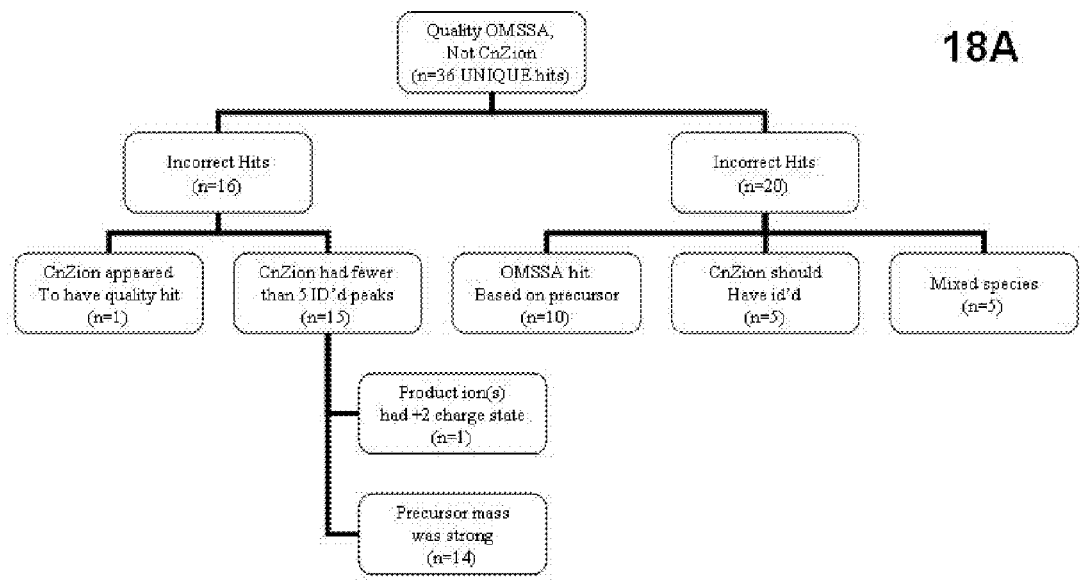
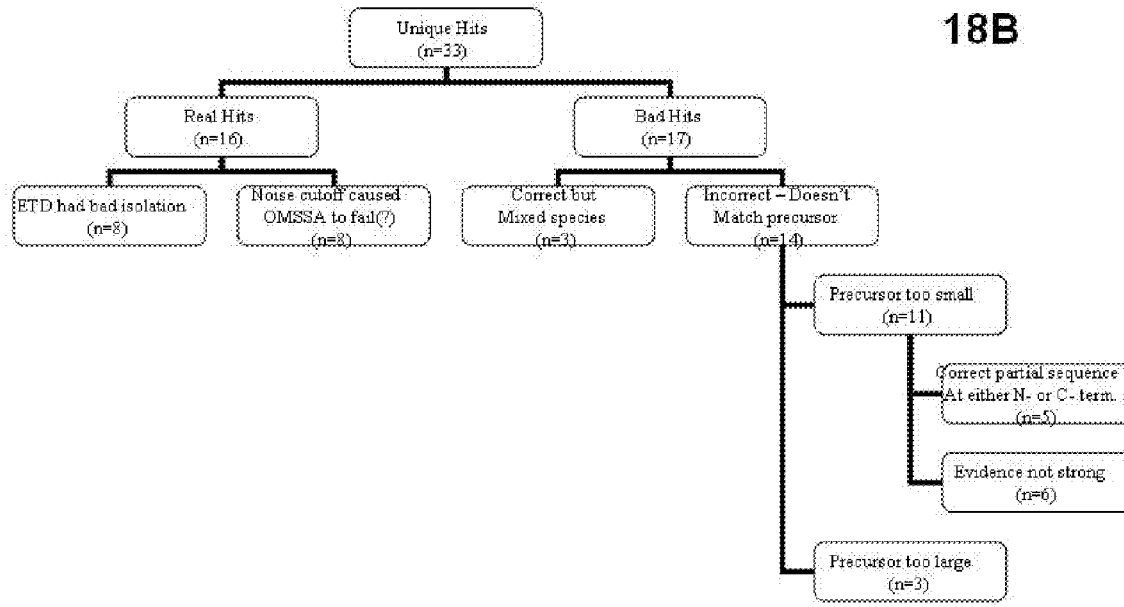
Figure 18

Figure 20

METHODS FOR PROCESSING TANDEM MASS SPECTRAL DATA FOR PROTEIN SEQUENCE ANALYSIS

CROSS-REFERENCE TO RELATED APPLICATIONS

This application claims the benefit of U.S. Provisional Application No. 60/991,398, filed Nov. 30, 2007, which is specifically incorporated by reference.

STATEMENT REGARDING FEDERALLY SPONSORED RESEARCH OR DEVELOPMENT

This invention was made with United States government support under GM080148 awarded by the National Institute of Health. The United States government has certain rights in the invention.

BACKGROUND OF THE INVENTION

Mass spectrometry (MS) is commonly used to provide information related to protein composition and peptide sequence. As efforts shift from sequencing the genome to understanding and identifying expressed genes and protein function, it is increasingly important that analytical tools be developed for providing reliable and rapid protein sequencing. Such protein sequence information can be used in proteomic databases and for identifying, understanding and using sequence information in a wide range of applications from fundamental research to medical treatment. The systems and methods disclosed herein provide improved tools for protein sequencing by increasing reliability and decreasing the experimental time required to analyze protein samples.

Proteins are involved in nearly every aspect of cellular function. In fact, the characterization of proteins has become such a significant part of modern biology, it has inspired a new discipline: Proteomics—the classification of the protein complement expressed by the genome of an organism. Technology development has, and continues, to drive rapid evolution in this field. Over the past several years many mass spectrometry (MS)-based protein identification strategies have emerged. Technical developments in chromatography and MS instrumentation have made two types or protein sequencing methods popular: (1) bottom-up and (2) top-down. For the bottom-up approach, a protein-containing sample is digested with a proteolytic enzyme resulting in a complex mixture of peptides. Next, the digested sample is chromatographically separated (in one or multiple dimensions) and introduced to the mass spectrometer by means of a nanoflow—high performance liquid chromatography column (nHPLC, ~50 mL/min) integrated directly to an electrospray ionization (ESI) source on the mass spectrometer. The ESI source converts condensed phase ions, eluting from the HPLC column, to multiply-protonated molecules (cations) in the gas-phase—a requirement for MS analysis. The mass spectrometer first records the mass/charge (m/z) of each peptide ion and then selects the peptide ions individually to obtain sequence information via tandem mass spectrometry (MS/MS). In a typical shotgun proteomics experiment a cell lysate, containing as many as several thousand proteins, is analyzed. In the top-down method intact proteins are ionized and directly sampled by the mass spectrometer and then fragmented during MS/MS analysis Tandem mass spectrometry is a method whereby peptides undergo the process of ion fragmentation with subsequent m/z measurement. Ion fragmentation for peptide and protein sequence analysis, with RF 3D quadrupole ion traps (QIT), quadrupole time-of-flight (Qq-TOF), and RF linear multipole ion trap (QLT) instruments, is generally performed via collision-activated dissociation (CAD). In this process, peptides that are protonated more or less randomly on backbone amide nitrogen atoms are kinetically excited and undergo collisions with an inert gas such as helium or argon. During each collision, imparted translational energy is converted to vibrational energy that is then rapidly distributed throughout all covalent bonds (ca. psec timescale). Fragment ions are formed when the internal energy of the ion exceeds the activation barrier required for a particular bond cleavage. Fragmentation of protonated amide bonds affords a homologous series of complementary product ions of type b and y. Subtraction of the m/z values for the fragments within a given ion series that differ by a single amino acid, affords the mass, and thus the identity of the extra residue in the larger of the two fragments. The complete amino acid sequence of a peptide can be directly deduced (de novo interpretation) by extending this process to all homologous pairs of fragments within a particular ion series.

Electron transfer dissociation (ETD) is a more recent technology for peptide fragmentation. Rather than using collisions, ETD reacts the selected peptide cations with anions of fluoranthene (or other negatively charged small molecules). This reaction proceeds by transfer of an electron from the fluoranthene anion to the peptide (an ion/ion reaction). The added electron causes the peptide to break randomly between each amino acid. Once the peptide is fragmented the masses of each fragment are then recorded. Unlike CAD, ETD causes cleavage of a different backbone bond to produce c and z-type fragment ions, rather than the b and y-type fragments generated by CAD. ETD can be considered a derivative of electron capture dissociation (ECD) which uses free electrons rather than anions to induce the same fragmentation pathways.

To date, ETD has been implemented on low resolution and mass accuracy mass spectrometers; however, we have recently modified a hybrid linear ion trap-orbitrap mass spectrometer to perform ETD (McAlister et al. Anal. Chem. 79(10) 3525-3534, 2007). This system routinely achieves 60,000 resolving power and measures the mass of ETD fragments to the third or fourth decimal place (low ppm to ppb mass accuracies). The current state-of-the-art bioinformatics approach to assigning peptide sequences to raw tandem mass spectra relies on spectral correlation methods. Yates and coworkers described a protein database/tandem mass spectral correlation algorithm (SEQUEST) in 1994. Since then numerous related programs have been reported. Each of these algorithms follows similar logic, with candidate peptide scoring and correlation being the major difference.

The common methodology involves: (1) pre-process the tandem mass spectrum, (2) compare precursor peptide mass to those obtained from an in silico protein digest, (3) score each sequence candidate's fit to the experimental spectrum, and (4) generate a scored output of sequences. Permutations of this strategy are mostly found in scoring step—Yates and colleagues have described the use of cross-correlation algorithms, while several newer methods utilize probability-based matching to calculate a matches statistical significance. Geer et al. have described one such method open mass spectrometry search algorithm, (OMSSA). In 1994 Mann and Wilm also introduced a notable variant of this approach called peptide sequence tag database searching. Here an algorithm attempts to extract partial sequence information directly from the tandem mass spectrum. The idea being most CAD tandem mass spectra do not contain complete backbone fragmentation, but small runs of 2-5 consecutive fragments (e.g., $b_2$, $b_3$, $b_4$,) are more likely to exist. This tag is then rastered along the predicted protein sequences of a predicted database. Once a matching sequence tag is identified from the database, neighboring residues are surveyed to determine a match. Advantages of this approach are increased probability to identify a priori unknown PTMs or potentially single amino acid substitutions. Generally, the sequence tag approach is not a widespread tool routinely used in high-throughput proteomics data analysis.

The current state-of-the-art techniques suffers from being relatively slow and computationally intensive, which in turn hinders real-time proteomic generation, identification and sequencing. They also require the candidate peptide sequence be predicted and present in the database. Techniques are needed that increase experimental speed and reduce computations to allow for real-time identification of unknown peptides during mass spectral analysis, while maintaining reliability. Real-time analysis provides additional capabilities such as intelligent data acquisition wherein an instrument makes automated decisions related to subsequent analysis. Reliable sequence assignment by mass spectrometry provides the capability of sequence determination without having to rely on additional database searching, including real-time sequence determination.

Information generated from the techniques, systems and methods disclosed herein have a range of uses, including but not limited to, commercial protein databases, algorithms related to searching of protein databases, which are of interest to mass spectrometer manufacturers and service providers, and for researchers using mass spectrometry for peptide sequencing and protein identification.

SUMMARY OF THE INVENTION

Peptide sequencing of proteins by mass spectrometry for protein identification and characterization is based on generating product ions from the protein. The product ions are detected by mass spectrometry, identified and analyzed. The identification of product ions are used as a basis for determining peptide sequences of the protein from which the product ions are generated. Depending on the technique used to generate product ions, there are many different classes of product ions depending on the location at which the protein or a fragment thereof breaks. Product ions that are z-type have a unique chemical composition in that they contain an even number of atoms with odd valence (N+H) compared to other relatively common product ions (e.g., b-, c- and y-type product ions). This provides the basis for the reasoning that no z-type ion has the same chemical composition for the generated companion ion (e.g., c-type product ion), or for the other major ion products that may be generated (e.g, b- and y-type). Accordingly, measuring the mass of a z-type product ion provides the capability of at least more reliably or uniquely identifying or classifying product ions. Increased confidence and reliability of product ion identification results in better downstream polypeptide or protein identification and therefore, better sequence information.

Other advantages of mass spectrometry systems that rely on z-type product ion identification include, but are not limited to, ultra-fast database sequence retrieval and scanning (e.g., on the order of loss than one second per scan), spectral sorting, sequence tag generation, real-time identification of unknown peptides (e.g., that are from a digest of a protein), intelligent data acquisition, reliable sequence assignments from mass spectra without necessarily relying on external database retrieval.

Appropriate selection of techniques for generating z-type product ions such as by ECD or ETD provides MS data containing a significant fraction of c and z-type product ions. Accordingly, annotating the z-type ions automatically provides information about the c-type ions. Labeling of the c and z-type ions allows for the elimination of noise peaks and the assignment of chemical composition and also permits sorting of good spectra from bad spectra. Exact chemical composition lists facilitates methodologies related to ultra-fast database sequence retrieval, spectral sorting, sequence tag generation, and de novo sequence analysis.

Furthermore, combining the methods with very high mass accuracy (ppm to ppb level) systems provides a fundamental shift to the protein sequencing bioinformatics (proteomics) approach. For example, with sufficient mass accuracy z-type product ions are distinguished from all other types of product ions. This ability to uniquely distinguish a single class of product ion types is the basis for use of novel algorithms related to amino acid composition and sequencing of proteins and peptide fragments thereof. With reliably identified and assigned c and z-type fragments, we bypass the shotgun strategy used by the conventional approaches. Any peaks not labeled c or z-type by the algorithm are immediately removed as they likely arise from noise so that a unique chemical composition to all labeled c and z-type ions is assigned. Any number of methods may be employed with the spectrally filtered data depending on the application of interest. A relatively straightforward and simple method involves aligning the observed chemical compositions with those existing in a protein database. The peptide sequence that generated the spectra is easily aligned with experimentally calculated chemical compositions to make peptide identification. This process is extremely fast and can be performed in less than one second per mass spectrum. Such speed accesses real-time data analysis during mass spectral acquisition. This capability transforms the types of information obtained from a proteomics experiment. In addition, the methods disclosed herein permit the direct determination of sequence from mass spectral data (de novo sequence assignment) and fast sorting of data into useful and non-useful spectra.

In an embodiment, the invention is a method for determining a composition of a polypeptide, such as a polypeptide generated from an enzymatic digest of one or more proteins or the intact protein itself. A polypeptide is introduced to a mass spectrometer, and more particularly the polypeptide is selectively fragmented to generate c and z-type product ions. The fragmentation is by any means known in the art, such as ECD or ETD, or any other method that generates c and z-type product ions such as via a chemically-driven process. z-type product ions are distinguished from the c-type product ions, such as by measuring the mass-to-charge ratio of the z-type product ions with the mass spectrometer. Putative chemical compositions are identified for at least a portion of the z-type product ions, c-type product ions, or both and the composition of the polypeptide is determined from the putative chemical compositions.

In another aspect, the mass of the z-type product ions, c-type product ions, or both is determined from the measured mass-to-charge ratio the z-type product ions or c-type product. For example, in those experiments where the product ions tend to have a charge of 1, the mass is equal to the measured mass-to-charge ratio. For experiments where a significant number of the peaks measured by the mass spectrometer have charge not equal to 1, algorithms known in the art convert mass-to-charge ratio to a mass. In this aspect, the mass at which the product ion is measure has a mass accuracy sufficient to distinguish the z-type product ions from the c-type product ions, such as a mass accuracy is better than or equal to 20 ppm, 10 ppm, 5 ppm, 2 ppm or 1 ppm. Although the particular mass accuracy is not critical in that methods presented herein have use over a wide range of mass accuracy, it is important that detected z-type product ions be capable of being distinguished from detected c-type product ions.

In an embodiment, the step of selectively fragmenting the polypeptide is carried out using electron transfer dissociation (ETD) or electron capture dissociation (ECD). In an aspect the mass spectrometer is a tandem mass spectrometer (MS/MS). In an aspect the mass spectrometer is an Orbitrap™.

In another aspect, identifying putative chemical is by providing an in silico database of the masses of all possible z-type product ions, c-type product ions, or both from all possible sequences of amino acids. In an aspect, the in silico database contains about 2,000,000 product ion masses, from all possible amino acid sequences less than about 2000 Da (corresponding to amino acid lengths or up to at most 34 residues). The mass of the product ion is compared against the in silico database to provide one or more chemical identification, referred herein as a "putative chemical composition" identification. The number of putative chemical compositions for a particular product ion may depend on the mass accuracy of the system. Accordingly, in an aspect the maximum size of the sequences of amino acids is less than or equal to 2000 Da.

In an embodiment, polypeptide composition determination is by de novo analysis. In another embodiment, polypeptide composition determination is by peptide or protein database searching. "De novo analysis" refers to composition determination such as protein identification without having to resort to a database of known protein sequences.

In another embodiment, any one or more putative chemical compositions obtained by any of the methods disclosed herein are used to search against amino acid compositions of peptides in a peptide database to identify putative proteins from which the polypeptide is derived. In this manner, it is possible to characterize and/or identify a protein from which the polypeptide is derived. Similarly, if multiple proteins are identified from which a polypeptide is derived, additional polypeptides may be sequenced and checked against the putative protein sequences or the instrument may be adjusted to selectively measure mass-to-charge ratios of product fragments that are expected to be generated from any one or more of the putative protein sequences.

In certain aspects, the invention relates identifying a measured mass product ion having a unique chemical composition of a single z-type fragment from all possible sequences of amino acids. Such unique identifications may be useful in the identification of tags that are then used to search against peptide databases or to identify product ions complementary to the "tagged" product ion.

Although any of the methods disclosed herein may be used with fragments that have any number of non-z-type product ion species, the methods rely on the presence of at least a detectable level of z-type product ions. In an embodiment, a majority of product ions generated in said step of selectively fragmenting said polypeptide are z and c product ions. In an embodiment, the step of selectively fragmenting produces a minority species of product ions that are not c and z product ions. Examples of such species include b- and y-type product ions and others known in the art. In an aspect, at least 50%, 65%, 70%, 80% or 90% of generated product ions (i.e., those that are the product of backbone cleavage) are c- and z-type product ions.

In another embodiment, any of the methods disclosed herein are for determining an amino acid sequence of the polypeptide. Determining the amino acid sequence of the polypeptide facilitates determination of the protein sequence from which the polypeptide is obtained. In an embodiment, the amino acid sequence is determined by reverse reading of the z-type fragments. In an embodiment, the amino acid is determined by forward reading of the c-type fragments Although any of the methods disclosed herein are for identification of a putative chemical composition of at least a single z-type product ion, in an aspect the invention identifies a putative chemical composition for all of the z-type product ions detected by the mass spectrometer. In another aspect, all the c-type product ions detected by the mass spectrometer are assigned a putative chemical composition.

For those methods where at least one product ion has an unambiguous candidate chemical composition, a chemical composition vector is generated. The chemical composition vector is optionally used as an identifier or tag for searching protein databases to assist in obtaining reliable protein identification.

An amino acid that has been post-translationally modified generates z-type product ions in a similar fashion to the z-type product ions generated by an unmodified amino acid. Accordingly, any of the methods are capable of use with a polypeptide having one or more amino acids that are post-translationally modified, such as a post-translational modification that is one or more of an acetylation, methylation, oxidation or phosphorylation, for example.

In another embodiment, any of the methods involves providing a proteomics database and searching the database against one or more of the putative chemical compositions to identify putative peptide sequences or proteins from which the polypeptide is derived.

Other aspects of the invention relate to different techniques and strategies for identifying product ions. For example, in scans where a product ion is not identified, a corresponding product ion that is identified with a putative or unique chemical composition may be used to provide identification of the not identified product ion. In this aspect, the identifying step relates to iteratively labeling unidentified ion products as c- or z-type product ions by comparing the unidentified product ions to one or more identified putative chemical compositions by determining a mass difference between unidentified higher mass spectrums compared to identified lower mass product ions. This mass difference can be searched against a database of possible amino acid chemical compositions to identify a missing amino acid sequence. Alternatively or in addition to the mass difference database search, gaps associated with the unidentified or missing product ions are identified by determining the total mass of the polypeptide and comparing the missing product ions against the determined composition. Gaps are filled by supplying the missing amino acid sequence so as to match the determined chemical composition.

Another aspect of the invention relates to reducing spectral noise so as to provide clean data sets for subsequent database searching to identify peptide sequences and for protein characterization or identification. In an aspect, this filter is used with any of the methods disclosed herein. For example, spectral noise may be reduced by identifying mass regions where all theoretically possible c and z-type product ions accumulate and eliminating as spectral noise those product ions with a mass-to-charge ratio having a mass outside the mass regions. It is particularly useful to reduce noise as that reduction can significantly reduce the computation and/or experimental time necessary for identifying composition of the polypeptide with sufficient accuracy. For example, the time required for determining polypeptide composition such as amino acid sequence may be reduced by one to three orders of magnitude compared to methods where spectral noise is not eliminated.

In another embodiment, the methods presented herein may be used to provide intelligent data acquisition, such as actively selecting fragments or product ions to be subsequently analyzed based on previously analyzed fragments or product ions. Methods are provided further comprising real-time adjustment of a mass spectrometer to provide intelligent data acquisition for subsequent fragment analysis. In a specific embodiment, this is accomplished by determining a putative peptide sequence based on a protein database search of the polypeptide composition. Knowledge of probable additional generated product ions based on previously identified fragments facilitates active searching for mass spectra peaks or product ions that meet the signature of any of the putative peptide sequences, thereby providing another means for reducing analysis time by further focusing efforts. From a putative protein or peptide selection, one or more z-type product ions that are capable of being generated from the putative peptide sequence are identified. This is used a basis for selecting a z-type product ion introduced to the mass spectrometer for subsequent analysis based on matching the selected z-type product ion with at least a portion of the putative peptide sequence.

In another aspect, methods are provided for assessing mass spectrum quality. In this aspect, spectra of low quality are ignored and efforts focused on analysis of good quality spectrum. This can also yield significant savings in protein identification and polypeptide composition determination. Spectrum data quality may be obtained by determining an allowable peak number, wherein the allowable peak number is the number of identified mass-to-charge product ions having at least one putative chemical composition and/or identifying a noise fragment number (which would depend on mass accuracy), wherein the noise fragment number is the number of mass-to-charge product ions having no putative chemical compositions. Any one or both of these numbers may be used as a basis for quantifying mass spectrum quality. For example, a mass spectrum may be rejected for further analysis for those spectra having a noise fragment number that is greater than or equal to a user-selected set value depending on mass accuracy. Similarly, a mass spectrum may be selected for further analysis if the spectrum has an allowable peak number that is greater than or equal to a user-selected value, such as three, for example. In an embodiment, mass spectrum data quality may be maximized by selecting a subsequent product ion for analysis for those fragments having said allowable peak number that is greater than or equal to three and excluding a subsequent product ion for analysis for those fragments having a noise fragment number that is greater than a user-selected set value depending on mass accuracy. Alternatively, an instrument parameter may be selectively adjusted to maximize or improve data quality. In an embodiment, the instrument parameter is one or more of: concentration of product ions; means for fragmenting said polypeptide; period of fragmentation; energy of fragmentation; number of anions used for ETD; type of mass analysis performed; selection of product ions for subsequent analysis.

Any of the methods disclosed herein may be used on polypeptides that are part of a mixture of polypeptide species. In this aspect, the plurality of polypeptide species may be efficiently identified by reducing spectral noise by identifying mass regions where all theoretically possible c and z-ion fragments accumulate. Accordingly, those fragments or product ions outside the identified mass regions and the remaining peaks separated into multiple lists of compatible peaks. "Compatible peaks" refers to those product ions that are compatible with each other (e.g., overlapping peptides in the sequence) or are capable of generation from an identical identified protein or polypeptide thereof. In an embodiment of this aspect the polypeptide amount in the sample is relatively low, such as on the order of femtomoles or less.

Alternatively, any of the methods disclosed herein may be used with a polypeptide that is an isolated and purified polypeptide. In another embodiment, any of the methods are used to identify fragments having a post-translational modification.

In another aspect, the invention relates to mass spectrometer calibration by identifying one or more product ions having a unique putative chemical composition and using the unique putative chemical composition as a calibrant to recalibrate the m/z assignment provided by the spectrometer. If a z-type product ion is uniquely identified, then the spectrometer, the data, or both can be reliably calibrated to that product ion.

In an embodiment, the invention is a method of real-time selection of polypeptides to be sequenced, from a sample containing one or more polypeptides by selectively fragmenting one or more polypeptides to generate c and z-type product ions. The mass-to-charge ratio is measured and the masses derived therefrom for at least a portion of the c-type product ions, the z-type product ions, or both at a mass accuracy sufficient to distinguish z-type product ions from c-type product ions. The resultant mass is compared to a database containing c-type ion product masses, z-type ion product masses, or both c-type and z-type ion product masses to identify matches. From the matches an at least a partial sequence of the polypeptide is obtained. From this partial sequence, the instrument can continuously select in real-time a polypeptide of the sample to be sequenced based on the matching step, wherein polypeptides are selected or excluded based on the previously at least partially sequenced peptide. This provides an additional data filter to further decrease experimental and analytical time.

Also provided are methods for calibrating a mass spectrometer by selectively fragmenting a polypeptide to generate c- and z-type product ions and measuring the mass-to-charge ratio of the c- and z-type product ions at a mass accuracy sufficient to distinguish said z-type product ions from said c-type product ions. At least one c or z-type fragment having a unique chemical composition is identified and the mass spectrometer is calibrated by adjusting an instrument parameter of the mass spectrometer so that calculated mass for the product ion having a unique chemical composition corresponds to the mass of the unique chemical composition. In an aspect this calibration step occurs during (e.g., real-time) or after the mass spectrometer operation. Optionally, the calibration is periodic, such as periodic calibration throughout mass spectrometry operation to ensure high reliability.

In another embodiment, any of the methods disclosed herein may be used to validate or identify deficiencies in a protein database by obtaining or providing a polypeptide high-probability amino acid sequence. This sequence is compared to a protein database and the database identified as deficient when the sequence cannot be matched to the database.

BRIEF DESCRIPTION OF THE DRAWINGS

FIG. 9 provides histograms of possible b/y-ion fragment masses (top) and c/z-ion fragment masses (bottom) for ion masses between 500 and 500.4. These data illustrate that b and y fragments frequently share the same chemical compositions while c and z ions do not.

FIG. 10 is an example of useful data generated by c/z-ion fragment by mass spectrometry for amino acid identification and sequencing.

FIG. 17 is a representative sample database search results compared to conventional OMSSA search.

FIG. 18 is a flow-chart summary of preliminary data comparing the use of identified c and z ions for sequence identification versus OMSSA, a benchmark database algorithm (A) and c/z ion methodology without OMSSA (B).

FIG. 20 is a summary of the analysis of c/z-type fragments from yeast used to determine a peptide sequence

DETAILED DESCRIPTION OF THE INVENTION

Figure 1:
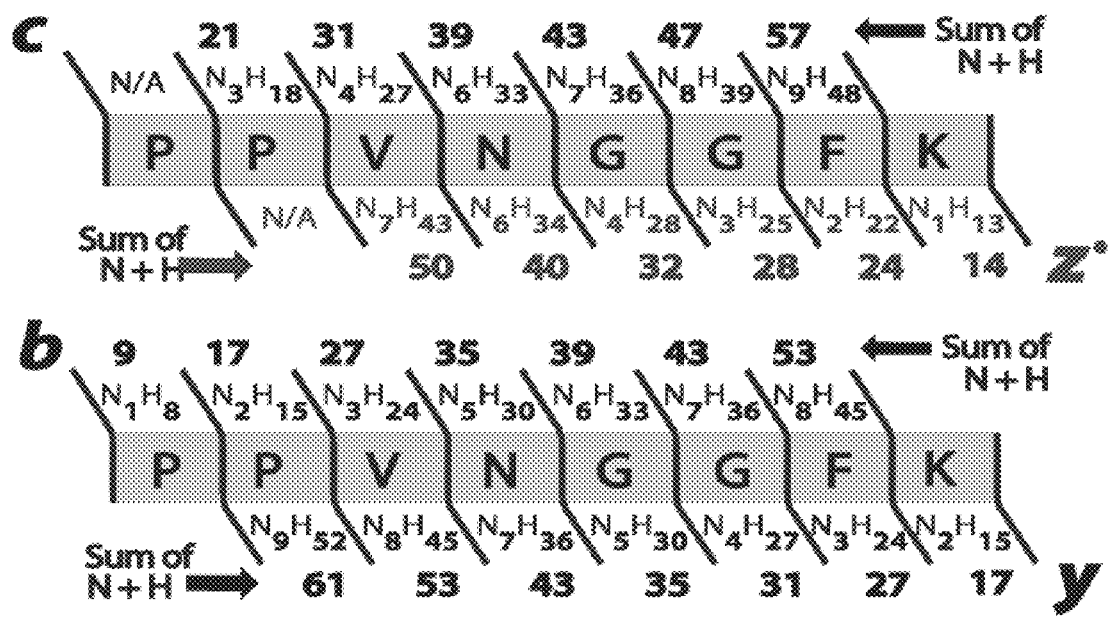
FIG. 1 summarizes the NH parity rule for an amino acid sequence PPVNGGFK. The top panel is c/z-type fragments and the bottom b/y-type fragments. The valence parity rule dictates that the sum of N and H atoms is always odd for c-type, b-type, and y-type ions and even for z*-type ions.

"Composition" refers to chemical information related to a protein or fragment thereof such as a polypeptide. In an aspect, composition refers to the relative amount of individual amino acids in a polypeptide. In another aspect, composition refers to the sequence of amino acids in a peptide sequence, such as at least a portion of a polypeptide sequence or protein sequence. Composition may also refer to detection or identification of one or more post-translational modifications to one or more peptides in the polypeptide or protein. The term "chemical composition" refers to the precise elemental composition comprising an m/z peak.

"Protein" refers to a molecule comprising multiple amino acids linked together via peptide bonds. The twenty amino acids genetically encoded in an organism's genome are the basic building blocks of proteins. Alternatively, the protein can be synthetically constructed or bioengineered. Each protein has a unique amino acid sequence, and so identification of a portion of a protein sequence can provide information as to protein identity. An amino acid may be chemically modified after expression by a mechanism referred to as "post-translational modification." For example, the amino-end of an amino acid is often acetylated, which makes the protein more resistant to degradation. Other examples include hydroxylation, carboxylation, methylation, oxidation and phosphorylation, among others. Although a protein may be of any length so long as the protein maintains biological activity, proteins are generally made up of more than about 50 amino acids.

"Polypeptide" refers to at least a portion of a protein, such as a protein fragment obtained from a protein digested by an enzyme. Accordingly, a polypeptide can encompass the entire protein length, or a contiguous portion of a protein. In an embodiment, the polypeptide has a smaller length than a protein, such as a length of about 10 to 20 amino acids. In an embodiment, the polypeptide is obtained by an enzymatic digest of a mixture of proteins isolated from a biological material or organism. For example, a complex biological sample can contain on the order of 1,000 proteins, with the digest yielding polypeptides having a typical length of about 10-20 amino acids, so that there may be on the order of 100,000 polypeptides to sequence. Accordingly, mass spectrometric analysis of the sequences of these polypeptides require computationally intensive algorithms to back-calculate protein sequences from polypeptide sequences. Optionally, the polypeptides may be at least partially purified and/or isolated by methods known in the art, such as by chromatographic methods, prior to introduction to the mass spectrometry detection.

"Fragmenting" refers to breakage of a polypeptide to generate charged species that can be detected by a mass spectrometer, thereby providing means for mass determination of the charged species. "Selectively fragmenting" refers to specifically breaking a polypeptide to ensure generation of a detectable and measurable amount of c- and z-type product ions. Other type of product ions may be generated, depending on the fragmentation means employed.

As used herein, "c-type" and "z-type" product ions refer to cleavage of peptides or polypeptides driven by free radical chemistry, such that the cleavage is directed to the $N-C_\alpha$ bond. The cleavage products are referred to as "product ions" or "fragments" that are classified as even-electron c-type fragments (N+H is even) and odd-electron z*-type fragments (N+H is odd). Other common fragments or product ions, such as "b-type" and "y-type" product ions may also be generated.

"Fragment" is used interchangeably herein with product ion. However, fragment may also refer to generation of smaller length polypeptides from a longer length protein. The polypeptides in turn are subjected to fragmentation means that generate smaller length product ions or charged fragments.

The basis of methods related to determining polypeptide composition relates to identifying z-type product ions and using the identified z-type ions to either directly determine polypeptide sequence or to identify other detected product ions. Accordingly, it is important that z-type product ions be distinguished from the c-type product ions that are generated along with z-type product ions. In an aspect, the distinguishing step is accomplished by measuring mass-to-charge ratio of a product ion to a sufficient mass accuracy to facilitate practical discrimination between a c-type and z-type product ion.

"Mass accuracy" refers to the certainty in which the determined mass corresponds to the true mass. In general, increased mass accuracy provides for more reliable identification of product ion by comparing the measured mass to a database of product ion masses and reduces the number of putative chemical composition matches and increases the likelihood of a unique chemical composition match. As recognized in the art, mass accuracy may vary with mass-to-charge ratio. In an aspect, mass accuracy refers to the mass accuracy at a specific mass-to-charge ratio. In an aspect, mass accuracy may be an average mass accuracy over a specific mass-to-charge ratio interval.

"Putative chemical composition" refers to assigning a detected product ion a probable chemical composition. For a fragmented polypeptide introduced to the mass spectrometer, the putative chemical composition of any number of product ions provides the ability to determine the composition of the polypeptide. In those applications where amino acid sequence is desired, composition determination may be direct (e.g., "de novo" sequencing), or in combination with database searching of "known" protein sequences.

"Database" is used broadly to refer to one or more of a fragment or product ion database, polypeptide sequences or protein sequences. Depending on the application, different databases may be used. "Proteomics database" refers to a database containing peptide sequences for proteins related to one or more biological organisms. Alternatively, the proteomics database can be based on a genomics database (e.g., nucleotide sequences) from which amino acid sequence is derived.

In an aspect, database refers to a database containing all possible product ions, particularly z-type product ions and c-type product ions. This database is readily generated in silico by computationally determining all possible amino acid sequences for a polypeptide up to a certain size, such as 2000 Da, for example. With all possible amino acid sequence, all possible z-type product ions and/or c-type product ions are computationally determined, based on the polypeptide breaking at different locations. This yields a database of masses and chemical compositions. Because of the unique chemical composition of z-type product ions, they tend to occupy unique mass regions with fewer overlapping masses attributed to other product ion types. Accordingly, when a product ion is experimentally detected and its mass calculated, the database can be used to provide a putative chemical composition associated with that product ion.

"Unique chemical composition" refers to those situations where a product ion has only one putative chemical composition. Those product ions having a unique chemical composition can be valuable in further identifying polypeptide or protein sequences and for polypeptide or protein identification.

"Chemical composition vector" (CCV) is used herein to denote product ions in a mass spectrum that are assigned a unique chemical composition. The CCV precisely describes one or more combinations of amino acids that comprise either the N or C-terminus of the peptide. Accordingly, those peaks with a CCV are not subject to uncertainty in assignment and can be used as an identifier or tag for searching protein databases to assist in obtaining reliable polypeptide or protein identification in a significantly reduced time.

"Spectral noise" refers to information obtained by the mass spectrometer that is not required for polypeptide composition determination. For example, spectral noise includes those m/z peaks that are not c- or z-type, or unwanted contaminants. Accordingly, methods that eliminate or substantially reduces spectral noise are useful to decrease experimental and analysis time.

"Real-time" refers to performing action based on data obtained during mass spectrometric operation or from subsequent analysis or database searching of data generated by the mass spectrometer. For example, scan rates of the methods disclosed herein can be on the order of 1 scan per second, sufficiently fast to permit results of that scan to influence or effect a change in how subsequent scans are conducted.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

EXAMPLE 1

Chemical Composition Vectors for Peptide Sequence Determination

This example demonstrates that the odd electron z*-type ions formed by the electron-based peptide dissociation methods (electron capture or transfer, ECD or ETD) have distinctive chemical compositions from other product ion types (e.g., b-, c-, and y-type ions). Specifically, b-, c-, and y-type ions have an odd number of atoms with odd valence (e.g., N and H), while z*-type ions contain an even number of atoms with odd valence. This tenet, referred to as the NH parity rule, mandates that no c-type ion shall have the same chemical composition, and by extension mass, as a z*-type ion. With experiment we demonstrate that nearly half of all observed c- and z*-type product ions resulting from 226 ETD product ion spectra (collected at a mass accuracy of 2 ppm) can be assigned to a single, correct, chemical composition and ion type by simple inspection of the m/z peaks (chemical composition vector, CCV). The CCVs provide: (1) a platform to directly determine amino acid composition, (2) an input for database search algorithms, or (3) a basis for de novo sequence analysis.

For over fifty years accurate mass measurements have provided a means to assign chemical composition to confirm structural assignments of synthetic or natural products.[1] Over this time mass spectrometric (MS) instrumentation has advanced greatly so that today such measurements are among the expected rigors of small molecule validation. The field of protein sequence analysis—proteomics—has likewise been accelerated by MS-based technologies, though derivation of peptide chemical compositions from mass alone is, generally, not possible. Zubarev, Marshall, and others calculate that with 1 ppm mass accuracy a unique chemical composition can only be determined for peptides having masses less than ~750 Da; 550 Da is the approximate limit for determining unique amino acid compositions—beyond this mass the number of isomeric possibilities increases exponentially.[2,3]

Tandem mass spectrometry (MS/MS) obviates this problem by providing a subset of sequence-specific product ions following dissociation of a selected precursor. Collision-activated dissociation (CAD) is the most commonly employed fragmentation method and generates b- and y-type product ions (fragments carrying either the peptide's N or C-terminus, respectively).[4] Direct sequence derivation (de novo) is accomplished by first deciphering which m/z peaks are b-type and which are y-type, and then reading the sequence either forward (b-type series) or in reverse (y-type series).[5] In practice, however, such assignments are difficult to make, even for high mass accuracy data sets—primarily because b- and y-type ions often share the same chemical composition (vide infra). Electron-based methods are also used for fragmentation, i.e., electron capture or transfer dissociation (ECD or ETD).[6,7] Cleavage in these methods is directed to the N—$C_\alpha$ bond, is driven by free radical chemistry, and generates even-electron c-type fragments and odd-electron z*-type fragments.

The unique cleavage observed from ECD/ETD prompted us to closely examine c- and z*-type fragment ion chemical compositions and to compare them to their b- and y-type kin. As such, we constructed a database consisting of all non-redundant peptide chemical compositions up to 1750 Da (considering all 20 amino acids, 2,027,790 entries). From these entries we tabulated the corresponding chemical compositions of the four fragment ion types for each (4,353,150 non-redundant entries). Through careful inspection of these formulae we noticed that z*-type fragment ions do indeed have distinctive chemical compositions. Specifically, b-, c-, and y-type ions have an odd number of atoms with odd valence (e.g., N and H), whilst z*-type ions contain an even number of atoms with odd valence (FIG. 1, see the proof and Table 1). More generally, the sum of the valences for all atoms comprising b-, c-, and y-type ions is odd and the sum of the valences for all atoms comprising z*-type ions is even.

Proof of NH parity rule:
Part 1: Let us notice that, according to the standard way of representing any amino acid graphically, where the nodes are atoms of H, O, S, N, C, and the edges are the chemical bonds, the following equation holds:

$$h+2o+2s+3n+4c = \text{twice the total number of chemical bonds},$$

where h=the number of H atoms, o=the number of O atoms, etc. The equation above follows from the observation that the sum $h+2o+2s+3n+4c$ represents the total number of bonds adjacent to all the atoms, and the result is twice the total number of chemical bonds because each bond joins exactly two atoms.

Therefore the number $h+2o+2s+3n+4c$ has to be even, which implies that $h+3n$ has to be even, which implies that $h+n$ has to be even.

Note that this property holds not only for amino acids, but for any neutral non-radical molecules. The general result is that the total number of odd valence atoms must be even.

Part 2: Now let us define the following notation: NH(x) is the number of nitrogen and hydrogen atoms in the object x. Then we can state the NH parity rule as NH(x) is Odd if x is a b-, c-, or y-ion fragment and
NH(x) is Even if x is a z*-ion fragment When computing the chemical composition of an ion fragment, there are two components: the collection of amino acids (residue masses) and a common modification, which we shall call the ion cap. For example, a c-type ion containing only glycine would have the chemical composition of the glycine residue ($O_1N_1C_2H_3$) plus the addition of the ion cap: one nitrogen atom and four hydrogen atoms (see Table 1). This sums up to $O_1N_2C_2H_7$. The z*-type ion equivalent of this example is more interesting because we must subtract a nitrogen atom and add one hydrogen atom and one oxygen atom, yielding $O_2N_0C_2H_4$ (the zero subscript is maintained for clarity).

More complex ion fragments would include more amino acids but only one ion cap. Therefore, the number of atoms of an element E can be represented as NH(ion fragment)=NH(ion cap)+NH(amino acid sequence)

The last term can be broken into its constituent parts:

NH(amino acid sequence)=NH(amino acid residue 1)+ . . . +NH(amino acid residue n)

The last column of Table 1 illustrates that NH(a) is even when a is an amino acid (this also follows from Part 1 above.)

Furthermore, using the fact that a sum of even numbers is always even,

NH(amino acid sequence)=Even+Even+ . . . +Even
=Even

Now we note that NH(c) is odd when c is the ion cap for a b-, c-, or y-type ion and is even for a z*-type ion (see bottom of Table 1). This gives us NH(x)=Odd+Even if x is a b-, c-, or y-type ion frag-ment
=Odd
NH(x)=Even+Even if x is a z*-type ion fragment
=Even This tenet, hereafter referred to as the NH parity rule, mandates that no c-type ion shall have the same chemical composition, and by extension mass, as a z*-type ion. In contrast, many b-type ions share their chemical compositions with y-type ions. For example, a b-type ion comprising the amino acids Pro, Pro, and Val has the same chemical composition as the y-type ion with Phe and Lys. This example indicates that every y-type ion that contains an Phe and a Lys could be confused with a b-type ion product (for more examples see Table 2). And, if only b- and y-type ions are measurable, it is possible for two different peptides to yield the same tandem mass spectrum (e.g., homeometric peptides).[8] FIG. 1 illustrates the confusion that can arise during peak assignment for CAD fragments as two of the b-type ions have the same chemical composition as y-type ions. Note the sequence, PPVNGGFK, is also homeometric with the sequence PPVGGNFK. The NH parity rule eliminates the possibility of homeometric peptides when considering c-type and z*-type ions with perfect accuracy.

Figure 2:
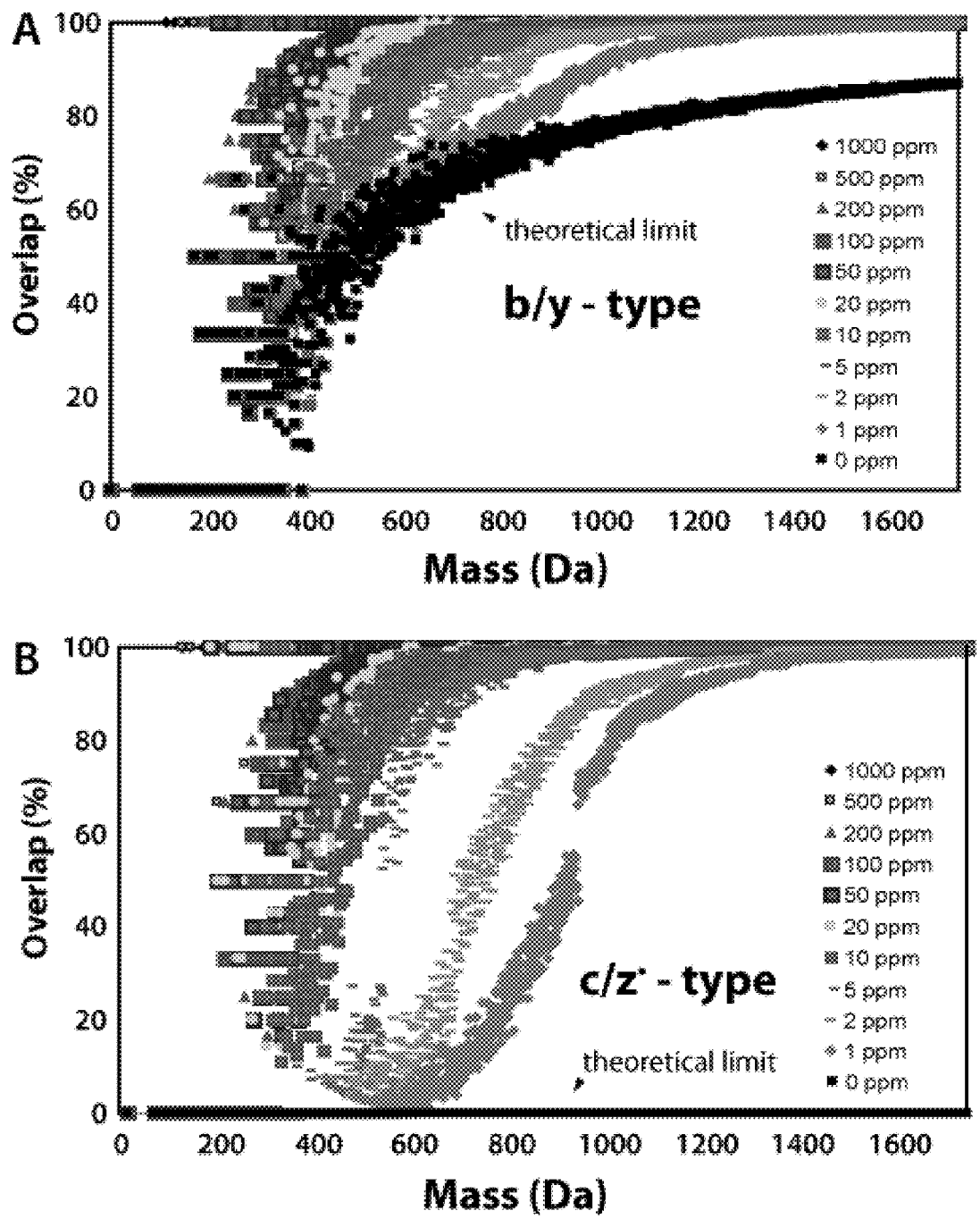
FIG. 2 contains graphs providing a comparative analysis of ambiguity in complementary ion pairs for b/y pairs (A) and c/z pairs (B).
Figure 3:
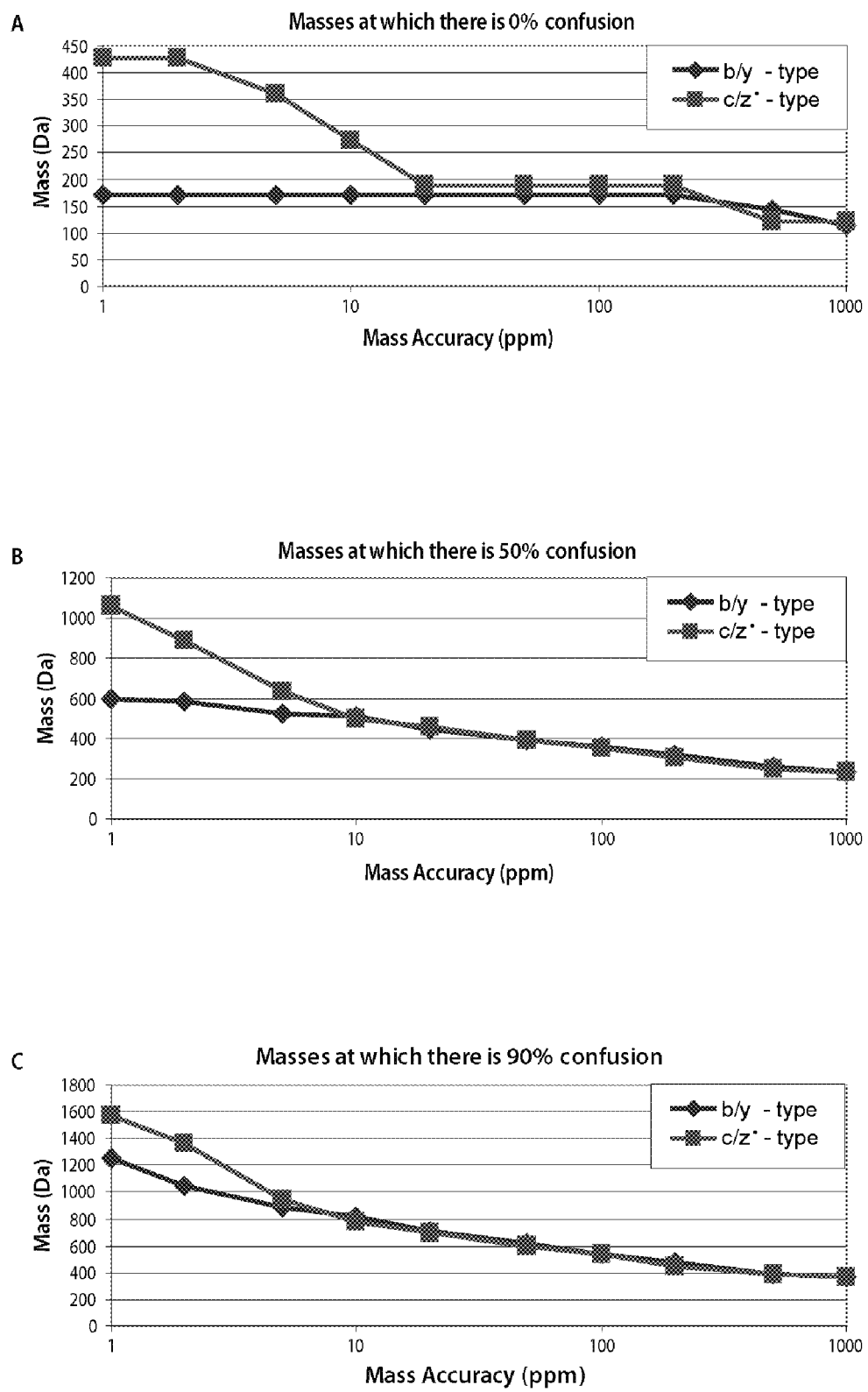
FIG. 3 illustrates the relationship between mass accuracy and certainty of peak assignment to ion type. A. The smallest product (mass, Da) for which there is an ambiguous assignment. B. The product mass (Da) at which the cumulative ambiguity of peak assignment is 50%. C. The product mass (Da) at which the cumulative ambiguity of peak assignment is 90%.

To determine the probability of unambiguous product ion-type assignment for either CAD or ECD/ETD spectra we plotted the frequency at which ion pairs (i.e., b/y- or c/z*-type, all possible unordered amino acid compositions) could be separated as a function of fragment size at various mass accuracies (FIG. 2). The black curves shown in FIG. 2 demonstrate the point made above—with perfect mass accuracy c- and z*-type ions are always distinguished (see FIG. 2B, where the black curve is at an overlap of 0% for all masses, whereas in FIG. 2A the overlap is significant for masses greater than about 400 Da), while b- and y-type ions having masses greater than 600 Da share identical chemical compositions more than 50% of the time. The chemical distinction of z*-type ions, however, only becomes relevant if product ion masses are known to within 5 ppm (FIG. 2). FIG. 3 displays the first mass at which ion type assignment is ambiguous for various mass accuracies. Even for small b- and y-type ions perfect mass accuracy will often not improve the situation since b- and y-type ions frequently share chemical compositions. FIG. 3B shows that with 1 ppm mass accuracy 50% of all c- and z*-type ions at mass 1050 are unambiguously assigned, in contrast to 50% of all b- and y-type ions at mass of only 600.

Figure 4:
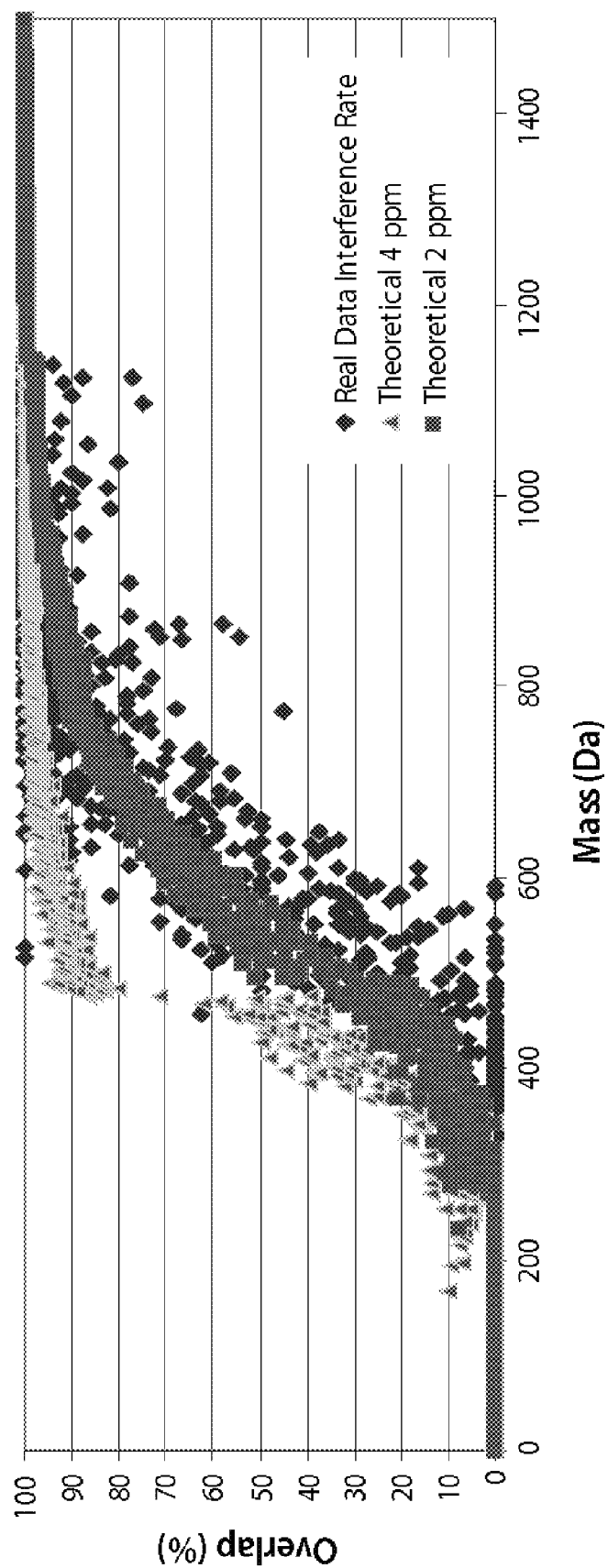
FIG. 4 Ambiguity of ion fragment assignments in the analysis of yeast peptides. The plot shows the percentage of peaks for which there is both a c- and a z*-ion fragment assignment for each mass (Da) using a window of 4 ppm. Theoretical accuracy curves for 4 ppm and 2 ppm are shown for reference. The fact that the data appears to match the 2 ppm theoretical results instead of the 4 ppm (as might be expected) can be explained by the fact that half of the measured mass values will fall on the far-side of the true mass from the peak that may confound the detection.
Figure 5:
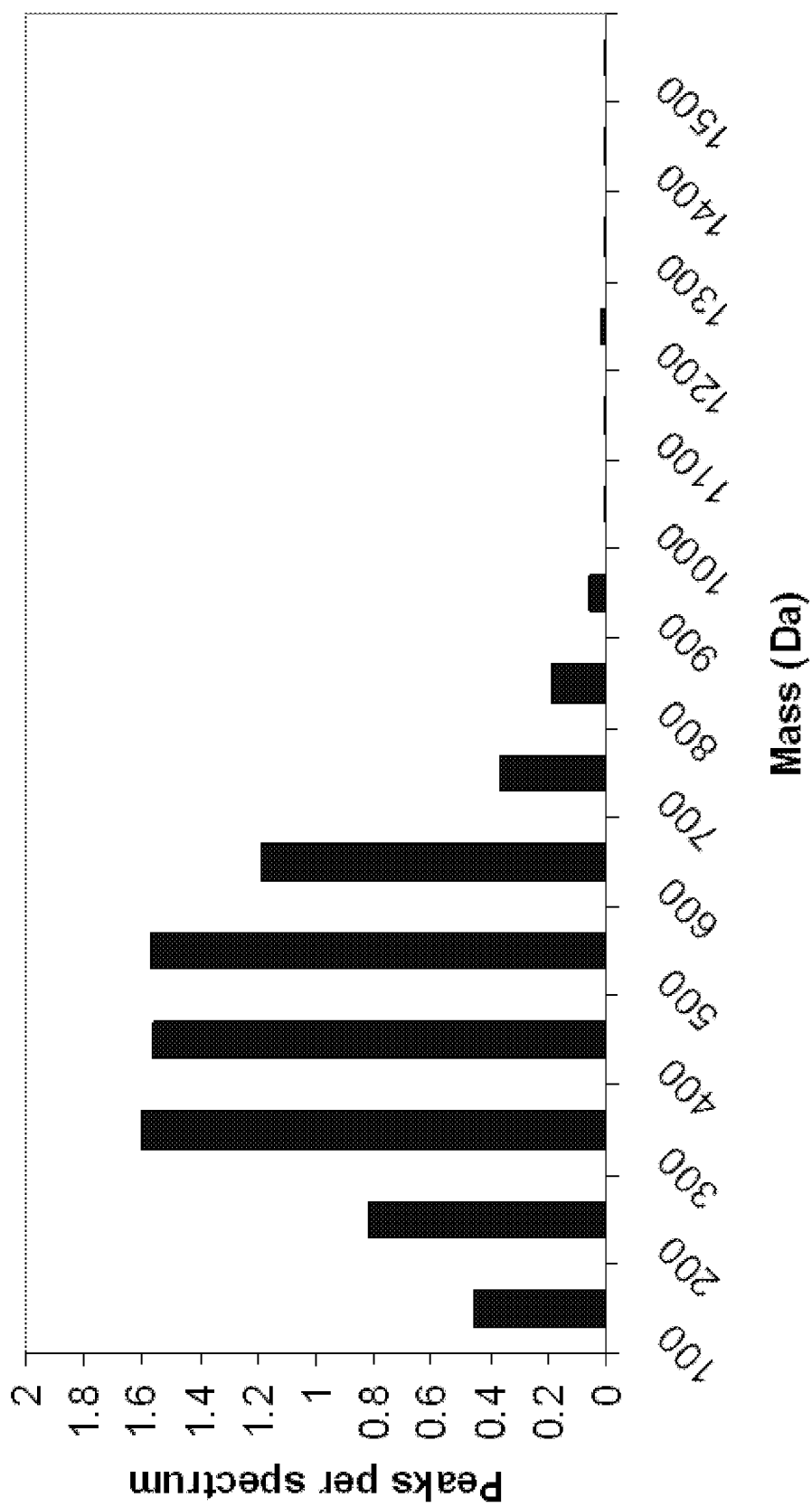
FIG. 5 Average number of chemical composition vectors (CCVs) per spectrum within each 100 Dalton range.
Figure 6:
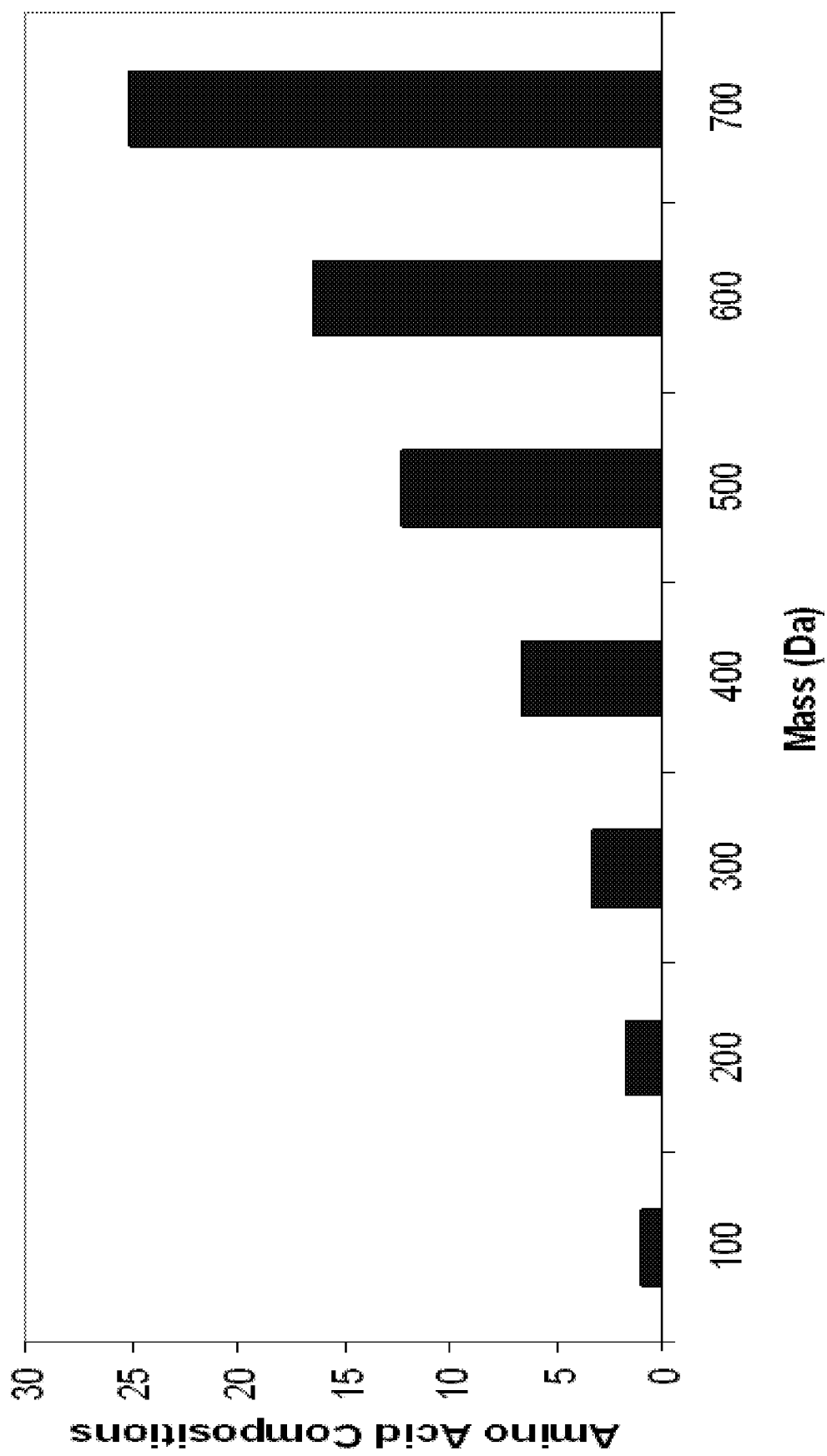
FIG. 6 Average number of amino acid compositions per CCV.

ECD tandem mass spectra are nearly always acquired by Fourier transform ion cyclotron resonance mass spectrometers (FT-ICR-MS) where achieving 1 ppm mass accuracy is routine. Recently, we have adapted a hybrid linear ion trap-orbitrap mass spectrometer to perform ETD reactions and have demonstrated its ability to measure c- and z*-type product ion masses to within 2 ppm.[9] (see also FIG. 7) Using our ETD-enabled orbitrap we tested our theory by examining 226 single-scan ETD-MS/MS spectra for ion type and chemical composition assignment. The spectra resulted from a single nanoflow-LC-MS/MS analysis of a complex mixture of yeast peptides (endo-LysC digest). Prior to examination, sequences had been assigned to each of the 226 spectra with high confidence using a database correlation algorithm. Manual inspection of these spectra confirmed the presence of 1962 distinct c- and z*-type ions with a signal-to-noise ratio greater than 2:1. Using a 4 ppm window, we could identify one or more candidate chemical compositions for 92% of these m/z peaks (1,812), with 48% given an unambiguous chemical composition and ion-type assignment (937 peaks). In such cases, i.e., when a peak can be assigned to a single chemical composition and ion type, we generate a chemical composition vector (CCV). The CCV, therefore, precisely describes one or more combinations of amino acids that comprise either the N or C-terminus of the peptide. FIG. 4 displays that the ambiguity rates for these experimental data closely correlate with theory. Next, we examined the number of CCVs assigned per spectrum at various masses (Da, FIG. 5). On average, each spectrum contained 8.0 chemically identifiable peaks, for which 4.1 had a corresponding CCV, with masses ranging from 100 to 1500 Da. We then computed the average number of unordered amino acid compositions that could result from the CCV and plotted this number for CCVs ranging in mass from 100-800 (FIG. 6). From these data we conclude that for even relatively high mass CCVs (e.g., 700 Da), there exists no more than 30 possible amino acid compositions. Of course, the presence of four CCVs per spectrum allows one to rapidly scan these short lists for common amino acid combinations or to assign the previously ambiguous peaks.

Post-translational modifications (PTMs) of amino acid side chains occur frequently and, in principle, could disrupt the NH parity rule. We examined four common PTMs—acetylation, methylation, oxidation, and phosphorylation—and verified that the NH-parity rule holds for all of them. And, because it is defined by valence parity, we reason the rule will hold for all modifications.

Chemical derivatization of the N or C-terminus and, more recently, the collection of sequential tandem mass spectra have been proposed as methods for ion type assignments.[10,11] Here we present a more expedient and direct route—namely, that the major product ions formed from ETD and ECD are chemically distinct, regardless of amino acid composition or the presence of common PTMs. This difference becomes relevant, and exploitable, at mass accuracies better than 5 ppm. With experimental data we show that nearly half of all peaks attributable to c- and z*-type ions can be assigned a CCV. The CCVs provide: (1) a platform to directly determine amino acid composition, (2) an input for database search algorithms, or (3) a basis for de novo sequencing. Finally, by restricting candidate m/z peaks in spectral processing to only those with CCV assignment one can essentially eliminate spectral noise (either chemical or electronic) from consideration and, in turn, dramatically increase the speed and accuracy of sequence assignment.

(1) Gross, M. L. *J. Am. Soc. Mass Spectrom.* 1994, 5, 57-57.
(2) Zubarev, R. A.; Hakansson, P.; Sundqvist, B. *Anal. Chem.* 1996, 68, 4060-4063.
(3) He, F.; Emmett, M. R.; Hakansson, K.; Hendrickson, C. L.; Marshall, A. G. *J. Proteome Research* 2004, 3, 61-67.
(4) Roepstorff, P.; Fohlman, J. Biomed. *Mass Spectrom.* 1984, 11, 601.
(5) Hunt, D. F.; Yates, J. R.; Shabanowitz, J.; Winston, S.; Hauer, C. R. *P Natl Acad Sci USA* 1986, 83, 6233-6237.
(6) Zubarev, R. A.; Kelleher, N. L.; McLafferty, F. W. *J. Am. Chem. Soc.* 1998, 120, 3265-3266.
(7) Syka, J. E. P.; Coon, J. J.; Schroeder, M. J.; Shabanowitz, J.; Hunt, D. F. *P Natl Acad Sci USA* 2004, 101, 9528-9533.
(8) Frank, A. M.; Savitski, M. M.; Nielsen, M. L.; Zubarev, R. A.; Pevzner, P. A. *J. Proteome Research* 2007, 6, 114-123.
(9) McAlister, G. C.; Phanstiel, D.; Good, D. M.; Berggren, W. T.; Coon, J. J. *Anal. Chem.* 2007, 3525-3534.
(10) Nielsen, M. L.; Savitski, M. M.; Zubarev, R. A. *Mol. Cell. Proteom.* 2005, 4, 835-845.
(11) Tsybin, Y. O.; He, H.; Emmett, M. R.; Hendrickson, C. L.; Marshall, A. G. *Anal. Chem.* 2007, 79, 7596-7602.

Figure 7:
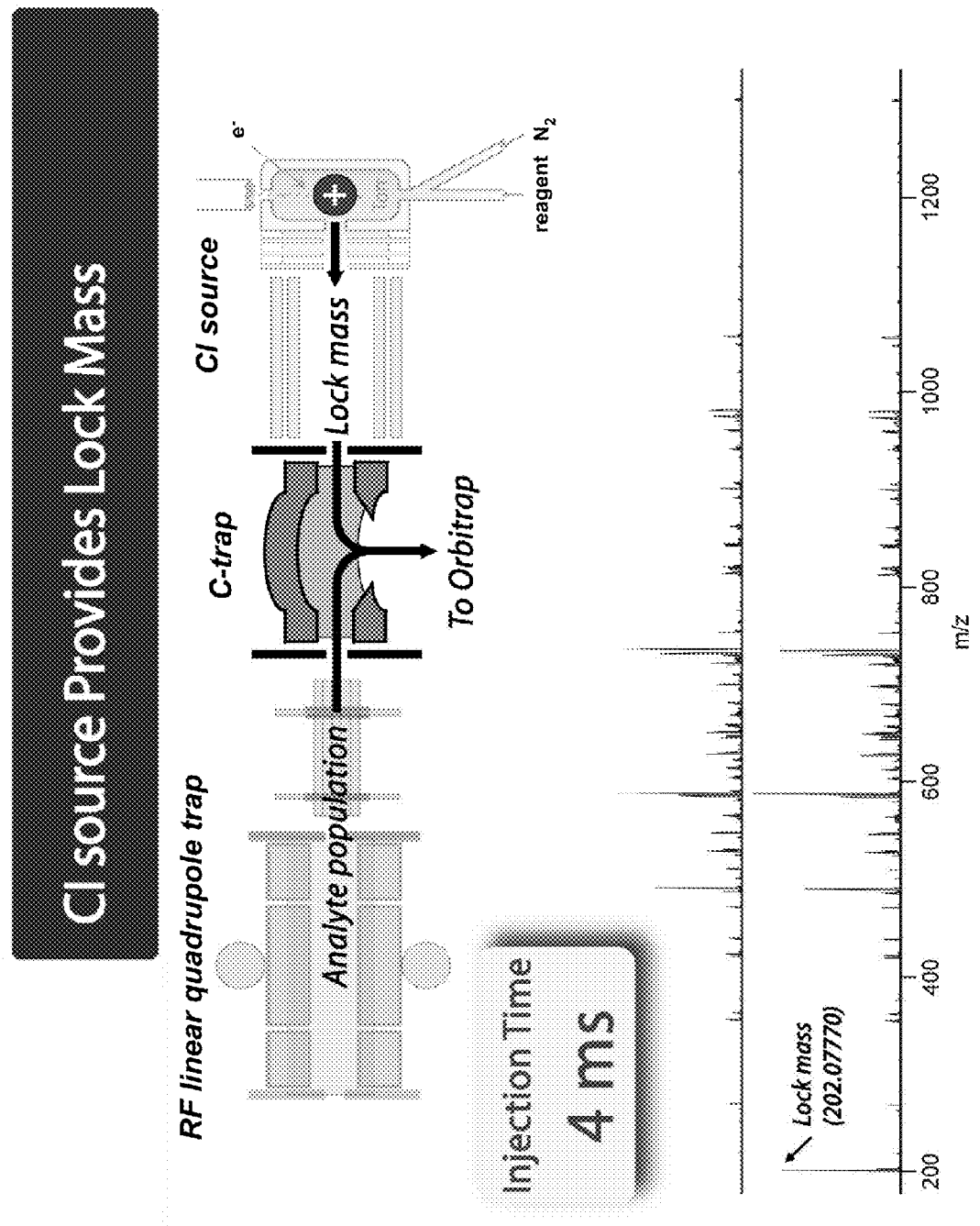
FIG. 7 is a schematic illustration of a tandem mass spectrometer where an analyte population undergoes m/z measurement by an orbitrap mass spectrometer. This schematic also shows how the injection of an internal standard (lock mass) can be added to a tandem mass spectrum in just 4 ms.
Figure 8:
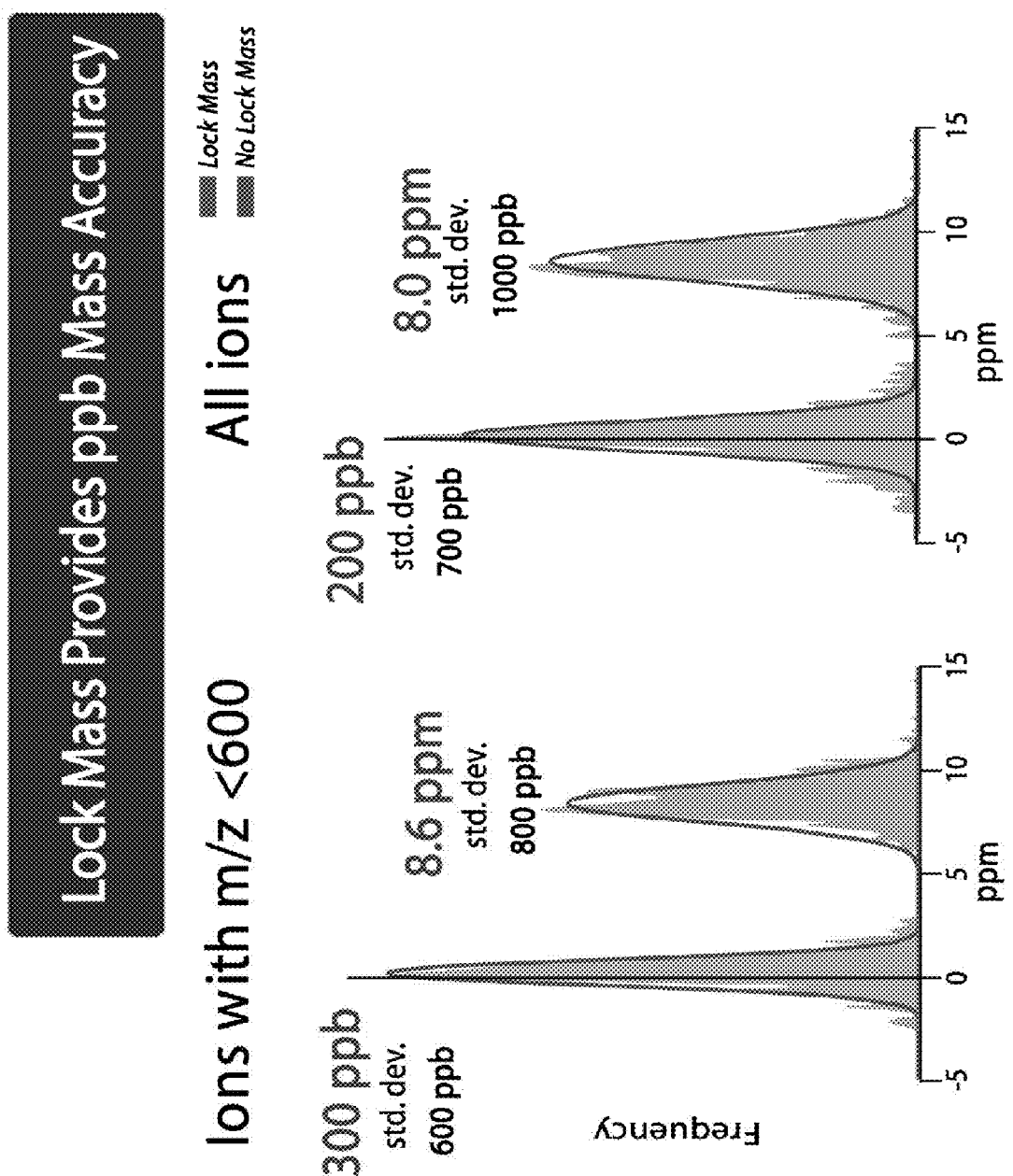
FIG. 8 illustrates that the lock mass provides ppb mass accuracies.

An example of an apparatus used to generate fragments capable of detection by mass spectrometry is schematically illustrated in FIG. 7. A Cl source provides lock mass to obtain ppb mass accuracy (FIG. 8).

FIG. 9 contains histograms of bin occupancy as a function of fragment mass for b/y-type fragments (FIG. 9A) and c/z-type fragments (FIG. 9B) for fragment mass between 500 and 500.4 from an in silico database of product ions. There are a significant number of bins occupied by both b and y-type fragments (FIG. 9A), whereas the bins occupied by c-ion fragments tend to be different than those bins occupied by z-ion fragments (FIG. 9B).

"Complementary ions" refers to that when a polypeptide is fragmented, a c and z-fragment pair (or similarly a b and y-fragment pair) is formed. Each member of the pair is referred to as the other's complementary ion or fragment. Accordingly, this complementarity may be used with algorithms as another variable for sequence generation and validity determination.

The detection and determination of c/z-type fragment mass provides the capacity to determine peptide composition or amino acid sequence of the digest, and thereby protein sequence of the starting material. An example of typical output from the methods and algorithms presented herein is provided in FIG. 10. Mass spectrometry of the c and z-type fragments, and information derived from the mass of those fragments, provides parameters related to total polypeptide mass, peak mass-to-charge, peak intensity, type of fragment, fragment mass, putative fragment identity, and the number of fragments that are capable of giving rise to a peak. In this example, the mass accuracy is 4 ppm (and at higher mass accuracies the number of identified fragments or putative chemical compositions attributed to a peak/ion product decreases). Each peak is analyzed and classified where applicable as arising from a c-type and/or z-type ion fragment and where possible assigned a chemical composition number for those peaks that can be assigned a putative fragment identity from a database containing possible c/z ion fragments. These putative identifications may be used in subsequent analysis (see FIG. 11) to determine amino acid compositions or sequences.

Figure 11:
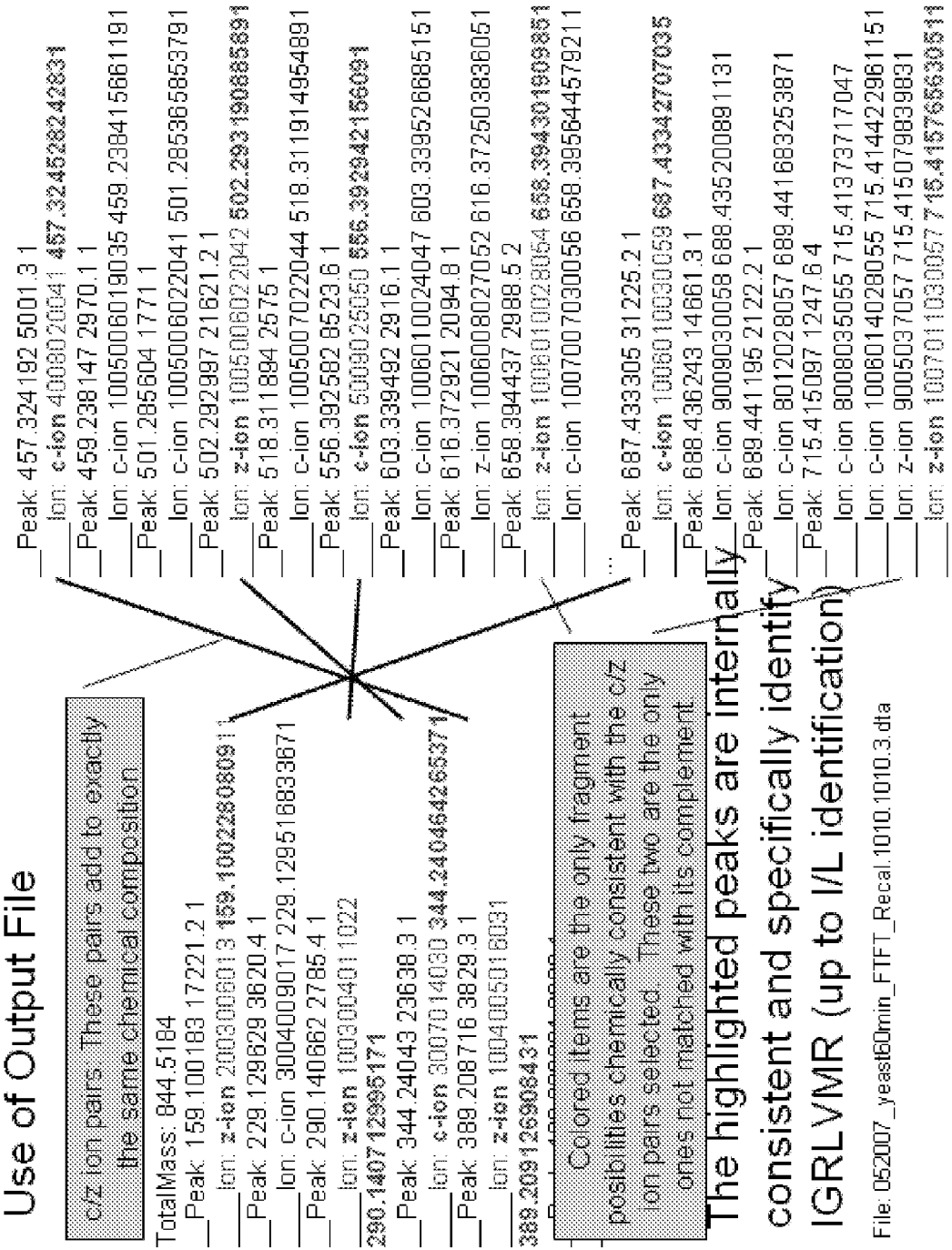
FIG. 11 illustrates use of the data of FIG. 12 to identify the polypeptide as having an amino acid sequence IGRLVMR.

The output file shown in FIG. 10 may be used for de novo sequencing (e.g., without using an external database of protein sequences) such as by complement fragment matching and assigning putative chemical identifications for internal consistency (FIG. 11). In this example, the putative chemical identifications for the fragments result in an amino acid sequence of IGRLVMR. Such sequence identification may be combined with other identified sequences from other polypeptide fragments to generate a protein sequence or used to as an input parameter to search protein sequence databases. Matched peaks provide a backbone of highly probable chemical compositions. The rest of the peaks can then be compared to the nearest matched peak of the same type. If the chemical difference between the peak being analyzed and the matched peak is not physically feasible (i.e. does not correspond to the sum of amino acids) the peak being analyzed may be removed. On the other hand, if there is a reasonable match, it will correspond with a likely interpretation of the peak as an unmatched peak.

Figure 12:
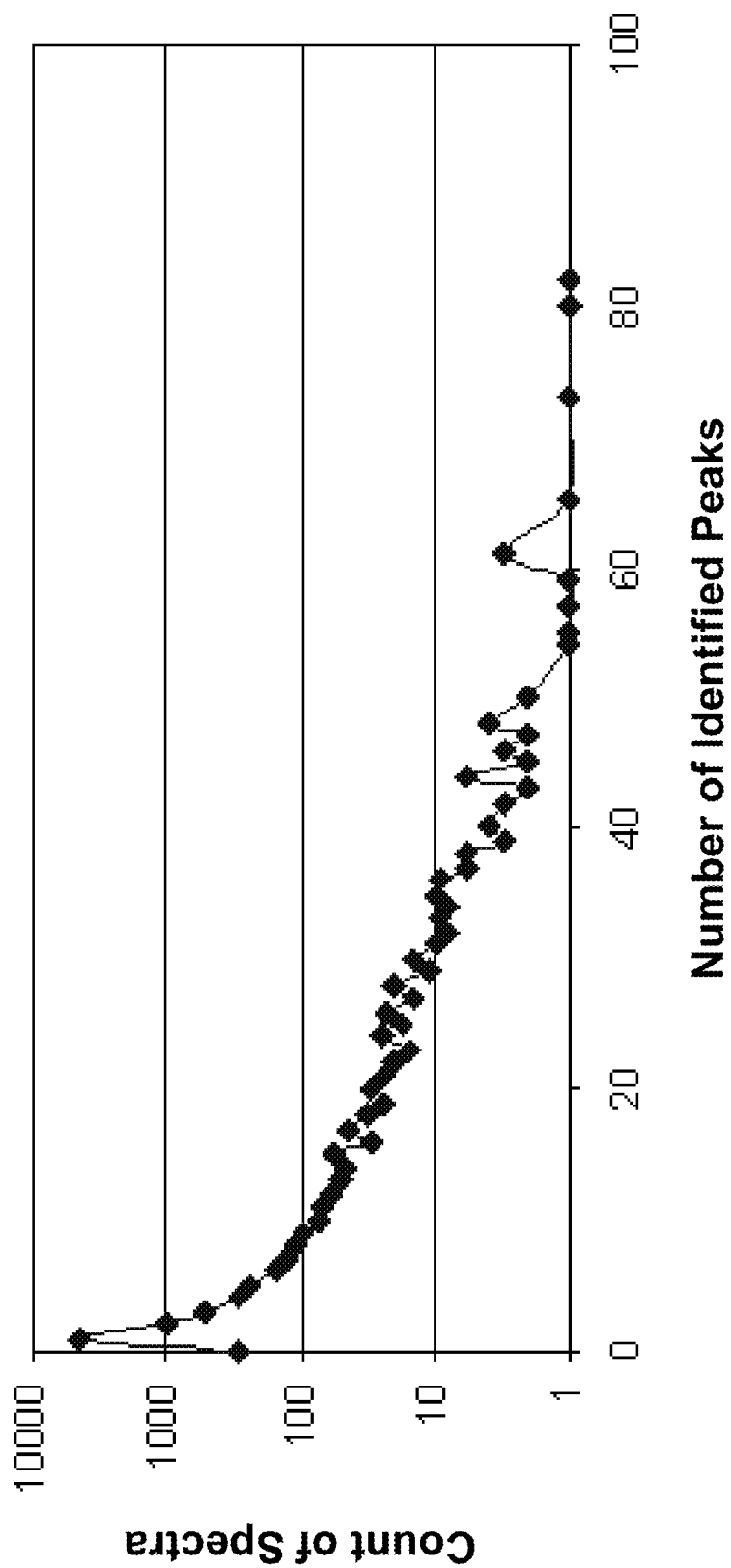
FIG. 12 Histogram of the number of identified peaks in a spectrum for a large data set.

In a given mass spectrometry experiment, a number of fragments are expected, corresponding to peaks in a mass spectrum. In general, the number of peaks identified as chemically meaningful is usually quite small (see FIG. 12). A small number of meaningful peaks probably reflect a "bad" spectrum. This provides a mechanism for filtering or removing bad spectra by requiring a minimum number of meaningful peaks. Requiring a spectrum to have a minimum of four possibly meaningful peaks eliminates approximately 75% of spectra, thereby further significantly reducing analysis time.

Figure 13:
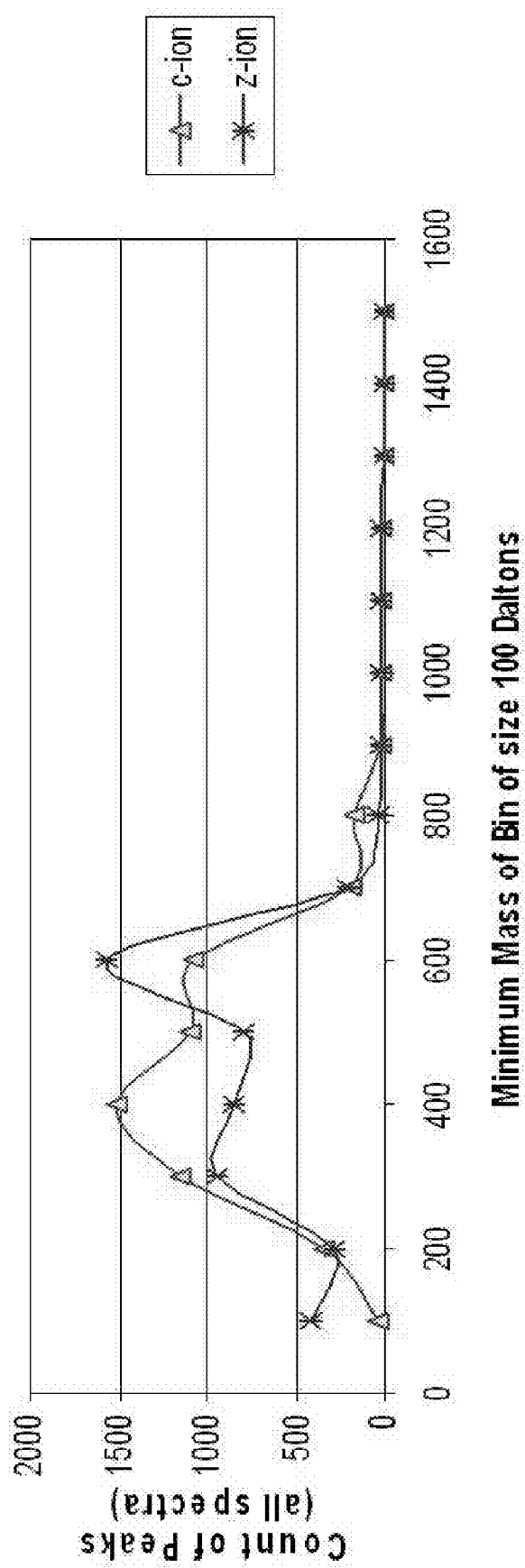
FIG. 13 Relative occurrence of unambiguous ions by mass by ion type.

A unique assignment of a particular fragment to a spectral peak is particularly useful because it reduces the complexity of identification, thereby increasing sensitivity and computation time for protein identification and sequencing. FIG. 13 reflects the relative occurrence of unambiguous peak assignments ("unique chemical composition") by region. For example, nearly one-quarter of all unambiguous peaks are in the range 600 to 700 Daltons. Beyond 700 Daltons unambiguous identification is difficult at 4 ppm (the resolution use for these analyses). Increased mass accuracy provides the capacity of increasing the size for which a unique or unambiguous chemical identification is possible.

Figure 14:
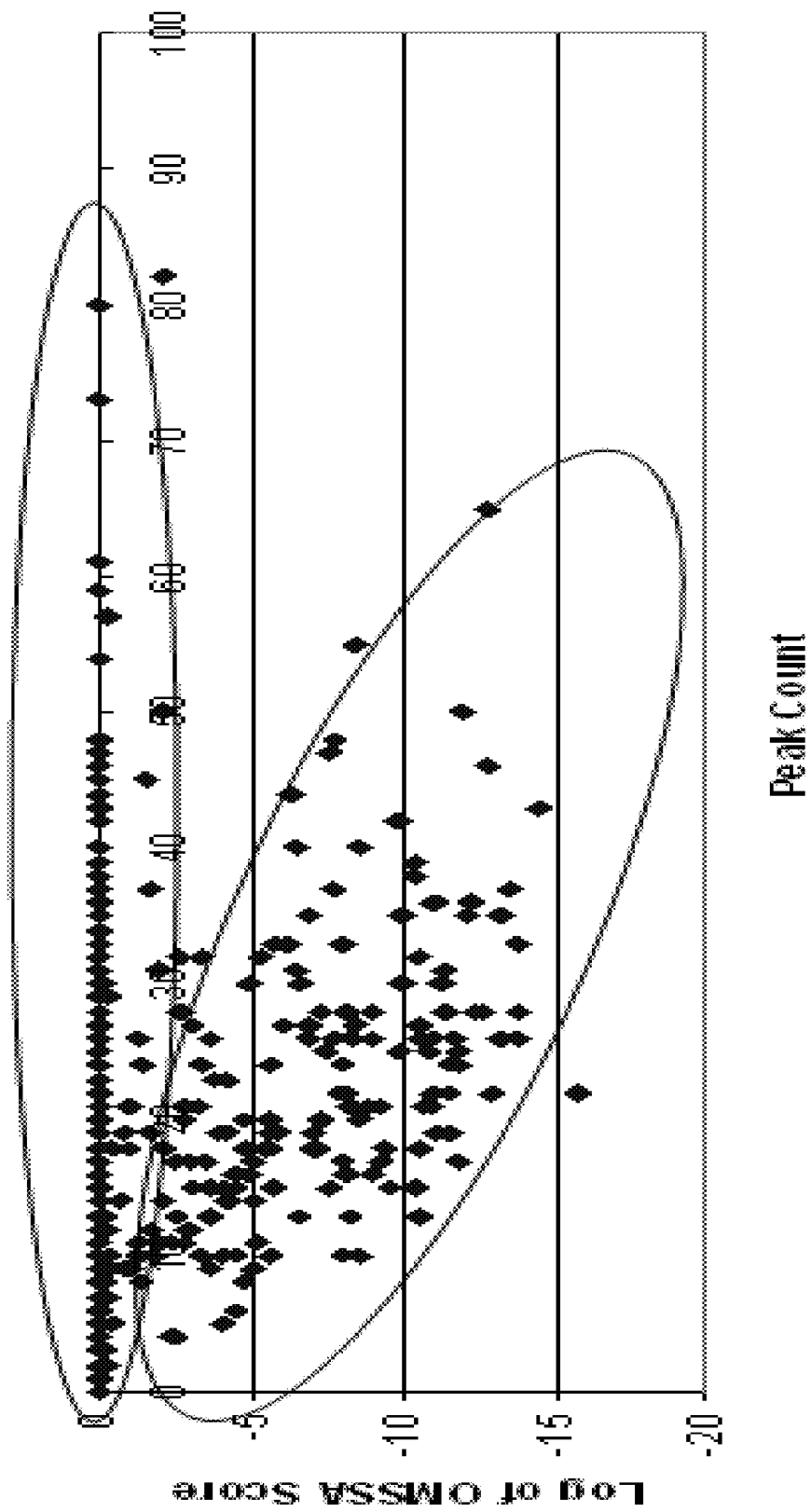
FIG. 14 Plot of the OMSSA score against the number of identified peaks. Here we see two clusters of data. The first show an improving OMSSA score with increased numbers of identifiable fragments. The second, however, shows that many spectra have large numbers of c and z ions, but do not result in an OMSSA matched peptide. This is presumably due to database deficiencies, indicating these spectra should be examined more closely.
Figure 15:
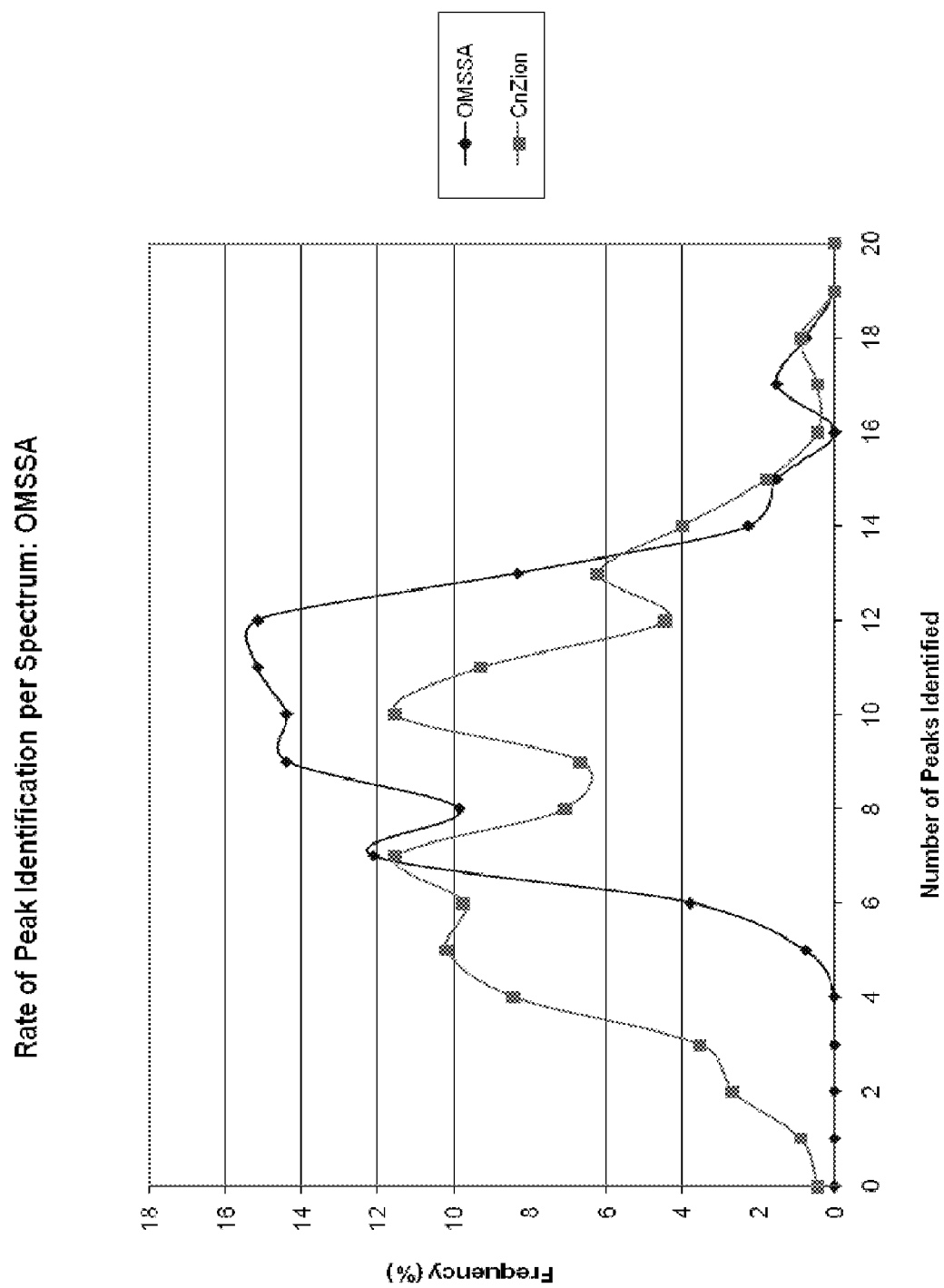
FIG. 15 Comparison of the histograms of the number of peaks identified for OMSSA (diamonds) versus the c- and z-type ions by the methods disclosed herein.
Figure 16:
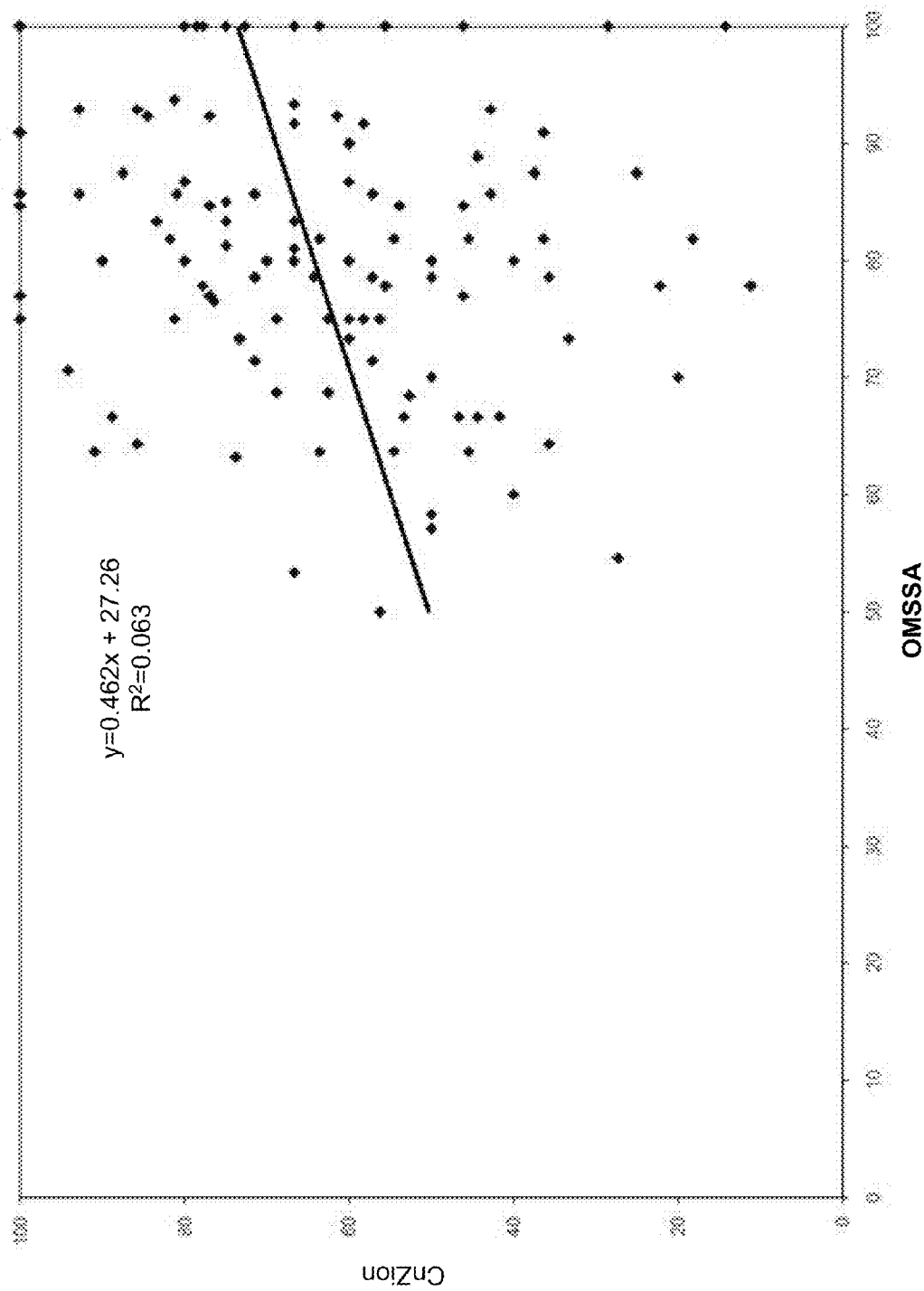
FIG. 16 Identification rate comparison for the c- and z-type ion method against the OMSSA method.
Figure 19:
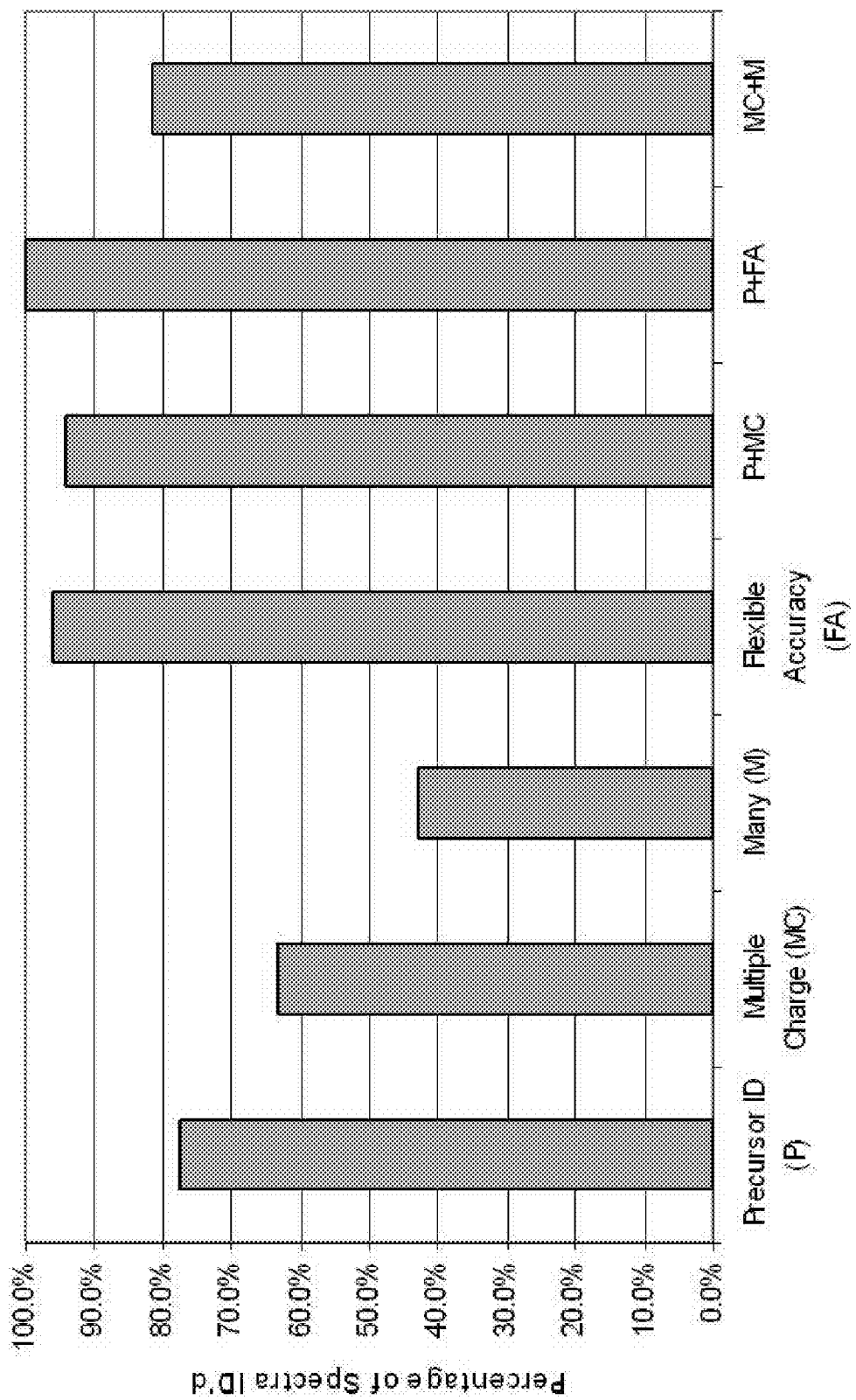
FIG. 19 Theoretical Changes to the above data processing methods to increase identification

A strong spectrum quality tool is useful for a number of reasons. For example, an obtained spectrum may be identified as "bad" and discarded thereby saving resources and analytical time. Resources and effort are instead focused on spectra identified as "good" quality. One simple marker of quality is the number of identified peaks (e.g., peaks having one or more putative chemical compositions). In order to evaluate number of identified peaks as a quality measurement, we compared the number of identified peaks with the OMSSA p-value (FIG. 14). Since OMSSA only identified 4% of the spectra, most of the datapoints are on the y-axis, indicating OMSSA did not identify any putative sequences. However, the appearance of two clusters suggests that there are several high-quality spectra that cannot be identified by OMSSA. A portion of the high-quality spectra are further manually examined to generally confirm they do include good spectra that reflect unexpected cleavages or mixed spectra. FIGS. 15-16 reflect that for OMSSA to identify an ion product, it must be present in the database. The present methods and systems, however, do not require the present of the peptide or protein sequence in a database in order to successfully identify a chemical composition.

EXAMPLE 2

Sequencing Via Database Searching

Although the methods provided herein are useful for de novo sequencing, they may also be used with database searching. This example illustrates a relatively simple database identification technique. Because we determine chemical composition and use that as an index in our databases, we can do a simple query to compare candidate or putative chemical compositions with those calculated in a database. We use a database formed from calculating a trypsin digest of yeast proteins. Because some of the OMSSA discovered peptides included missed cleavages, we supplement those to the database. Finally, we exclude all peptides longer than 50 amino acids. This left a total of 205,091 peptides. Next we calculate every possible ion fragment of these peptides (by chemical composition—there were only 42,962), keeping track of which peptides could produce which fragments (e.g., identical fragments are produced by different peptides). Finally, we scored each peptide by how many of its fragments were in common with the evaluated spectrum. The results are striking. Without allowing for the total mass or a large variety of other factors to improve accuracy (such as using the "Many" spectral matches), this algorithm produces one solution that was clearly the best and that matched OMSSA's best 57% of the time (see TABLE 3 and FIG. 17). For a spectrum to be classified as a poor quality spectrum, it should be devoid of c- or z-type ion product identification. Accordingly, a filter may be utilized to automatically identify poor quality spectrum, thereby avoiding unnecessary spectrum analysis. This filter may be based on a user-selected minimum number of c- and/or z-type ion products that are identified. In the present example, that number is currently five, but may be increased or decreased as desired.

TABLE 4 summarizes the results of successful amino acid sequence identification for a spectrum for three different analysis techniques (OMSSA; c/z ion; OMSSA and c/z ion). These data summarize a number of strengths of the c/z ion methods presented herein, including: (1) Readily distinguishing high from low quality spectra; (2) Performing 4847 analyses in 5 minutes, fast enough for the method to be used for real-time mass spectrometry analysis/adjustment; (3) Returned 97% OMSSA concordant results, when both methods gave a good result; (4) Returned fewer false results (results that could not be validated by visual inspection); (5) Successfully identified a peptide for 1.3% (59/2972) of spectra where OMSSA failed; (6) Could identify peptides without reference to existing peptide databases (e.g., de novo sequencing)

FIG. 18 provides a flow-chart summary of the OMSSA methodology results (FIG. 18A) and the c/z-fragment methodology (FIG. 18B) to provide information about the basis for the incorrect hits. These data demonstrate that OMSSA does not always identify spectra of high quality and that by first examining the data for c and z ions one can improve the number of peptides sequenced. It shows examples of where the database method must fail for a variety of reasons (e.g., presence of unsearched PTMs).

EXAMPLE 3

Amino Acid Sequencing

Figure 20:
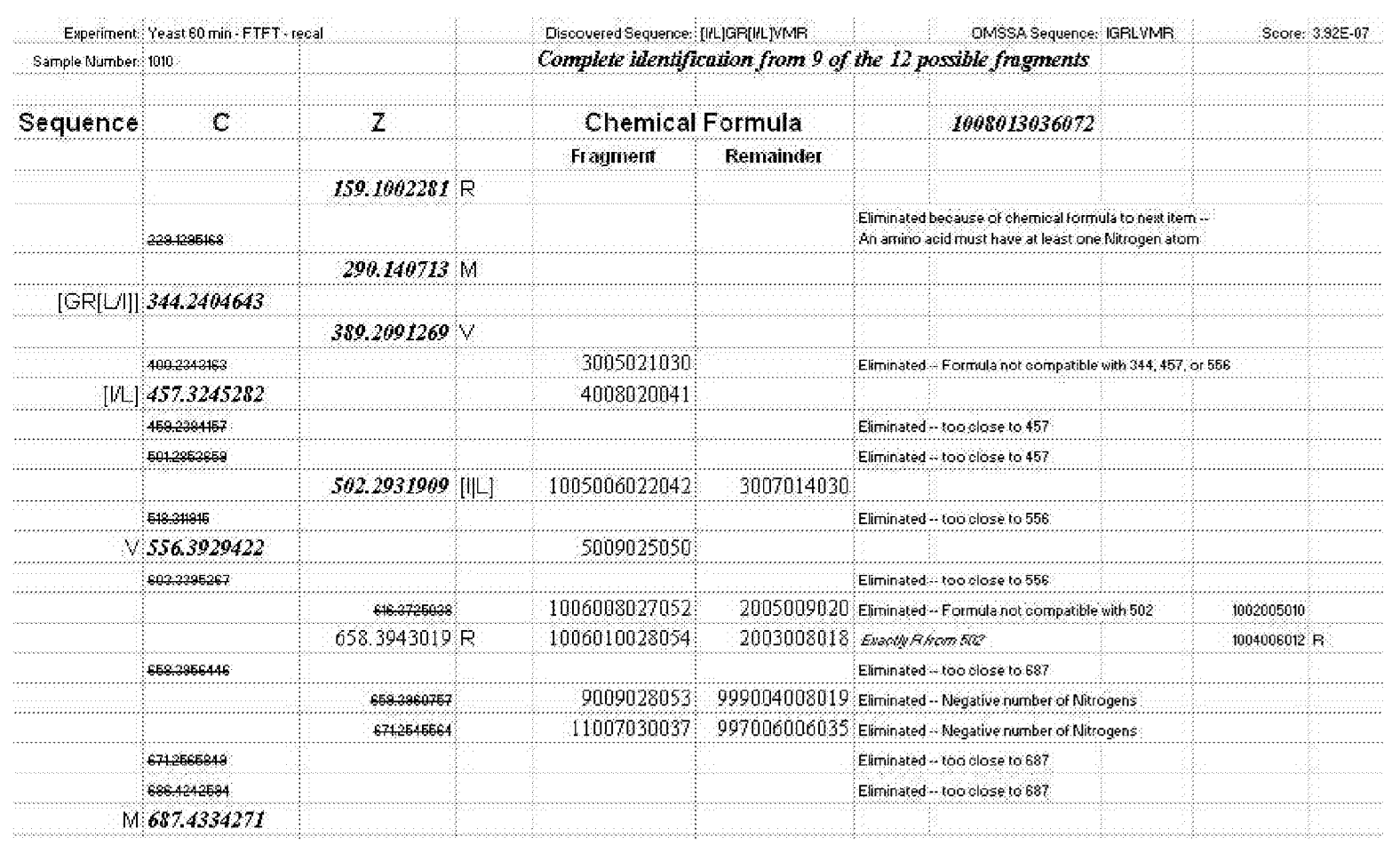

An example of sequence determination from detected fragments or a mass spectrum of c- and z-type fragments is provided in FIG. 20. Based on complete identification from nine of the twelve possible fragments (e.g., the entries that are not crossed out), the discovered sequence is [I/L]GR[I/L]VMR. OMSSA identified six possible sequences but the only one that had a good score (E=3.91695E-07), was IGRLVMR. [I/L] represents a well-known issue with de novo sequencing in mass-spectrometry: Leucine and Iso-leucine have the same chemical formulas, differing only in the arrangement of the atoms—it is not possible to distinguish them by mass alone. The data shows that some fragments are eliminated as too close to adjacent masses, not compatible with the other identified fragments, or as having a negative number of N and H. Some of the fragments are uniquely identified (see entry for R). The sequence obtained from the experiment summarized in FIG. 20 may be repeated for other relevant polypeptides, with the plurality of sequences used for de novo sequencing. Alternatively, or in addition, any of the sequences either alone or in combination may be used in a proteomic database search to assist in generating a protein sequence or for protein identification.

TABLE 2

List of amino acid combinations where the b-type ion fragment has the same m/z value (where z = 1) as a y-type ion fragment. This list only includes m/z peaks less than 500. Highlighted items are examples that are consistent with a tryptic peptide. The order of the amino acids is alphabetical to simplify sorting. The pairs are grouped by exact mass. This list only includes those pairs that cannot be derived from a pair with a smaller mass. The remaining 36,131 pairs are all similar to a pair listed below with the addition of an identical amino acid combination mass, such as adding GG to the b-type ion and N to the y-type ion (GG and N have the same mass).

| m/z | b-ion Sequence | y-ion Sequence |
|---|---|---|
| 173.092069 | AT | GP |
| 187.107719 | SV | AP |
| 203.102633 | TT | PS |
| 205.097154 | FG | W |
| 215.139019 | IT | PV |
| 215.139019 | LT | PV |
| 219.079790 | MS | CP |
| 231.097548 | ET | DP |
| 243.108781 | AGGG | HS |
| 243.108781 | AGN | HS |
| 243.108781 | GGQ | HS |
| 243.108781 | NQ | HS |
| 257.124431 | AAGG | HT |

TABLE 1

Chemical composition of individual amino acid residues and the atomic contribution of the four ion fragment types discussed in the text. Italicized entries illuminates the cases where the number of N + H is odd. An ion fragment consists of a collection of items from the top table and one item from the bottom table, so that z-type fragments have even N + H, and the other fragment types (c, b, y-type fragments) have odd N + H.

| Abbr | Amino Acid | Integer Residue Mass (mono-isotopic) | Accurate Residue Mass (mono-isotopic) | S | O | N | C | H | N + H |
|---|---|---|---|---|---|---|---|---|---|
| G | Glycine | 57 | 57.0214637 | 0 | 1 | 1 | 2 | 3 | 4 |
| A | Alanine | 71 | 71.0371138 | 0 | 1 | 1 | 3 | 5 | 6 |
| S | Serine | 87 | 87.0320284 | 0 | 2 | 1 | 3 | 5 | 6 |
| P | Proline | 97 | 97.0527638 | 0 | 1 | 1 | 5 | 7 | 8 |
| V | Valine | 99 | 99.0684139 | 0 | 1 | 1 | 5 | 9 | 10 |
| T | Threonine | 101 | 101.047678 | 0 | 2 | 1 | 4 | 7 | 8 |
| C | Cysteine | 103 | 103.009185 | 1 | 1 | 1 | 3 | 5 | 6 |
| L | Leucine | 113 | 113.084064 | 0 | 1 | 1 | 6 | 11 | 12 |
| I | Iso-leucine | 113 | 113.084064 | 0 | 1 | 1 | 6 | 11 | 12 |
| N | Asparagine | 114 | 114.042927 | 0 | 2 | 2 | 4 | 6 | 8 |
| D | Aspartic Acid | 115 | 115.026943 | 0 | 3 | 1 | 4 | 5 | 6 |
| Q | Glutamine | 128 | 128.058578 | 0 | 2 | 2 | 5 | 8 | 10 |
| K | Lysine | 128 | 128.094963 | 0 | 1 | 2 | 6 | 12 | 14 |
| E | Glutamic Acid | 129 | 129.042593 | 0 | 3 | 1 | 5 | 7 | 8 |
| M | Methionine | 131 | 131.040485 | 1 | 1 | 1 | 5 | 9 | 10 |
| H | Histidine | 137 | 137.058912 | 0 | 1 | 3 | 6 | 7 | 10 |
| F | Phenylalanine | 147 | 147.068414 | 0 | 1 | 1 | 9 | 9 | 10 |
| R | Arginine | 156 | 156.101111 | 0 | 1 | 4 | 6 | 12 | 16 |
| Y | Tyrosine | 163 | 163.063329 | 0 | 2 | 1 | 9 | 9 | 10 |
| W | Tryptophan | 186 | 186.079313 | 0 | 1 | 2 | 11 | 10 | 12 |

| Ion Type | Mass | S | O | N | C | H | N + H |
|---|---|---|---|---|---|---|---|
| c-ion | 18.0343741 | 0 | 0 | 1 | 0 | 4 | *5* |
| z-ion | 2.99966565 | 0 | 1 | −1 | 0 | 1 | *0* |
| b-ion | 1.00782503 | 0 | 0 | 0 | 0 | 1 | *1* |
| y-ion | 19.0183897 | 0 | 1 | 0 | 0 | 3 | *3* |

TABLE 2-continued

List of amino acid combinations where the b-type ion fragment has the same m/z value (where z = 1) as a y-type ion fragment. This list only includes m/z peaks less than 500. Highlighted items are examples that are consistent with a tryptic peptide. The order of the amino acids is alphabetical to simplify sorting. The pairs are grouped by exact mass. This list only includes those pairs that cannot be derived from a pair with a smaller mass. The remaining 36,131 pairs are all similar to a pair listed below with the addition of an identical amino acid combination mass, such as adding GG to the b-type ion and N to the y-type ion (GG and N have the same mass).

| m/z | b-ion Sequence | y-ion Sequence |
|---|---|---|
| 257.124431 | AAN | HT |
| 257.124431 | AGQ | HT |
| 257.124431 | QQ | HT |
| 262.103362 | SSS | ADG |
| 262.103362 | SSS | DQ |
| 262.103362 | SSS | EGG |
| 262.103362 | SSS | EN |
| 263.139019 | VY | FP |
| 276.119012 | SST | AAD |
| 276.119012 | SST | AEG |
| 276.119012 | SST | EQ |
| 294.181218 | PPV | FK |
| 303.166296 | KSS | AAAA |
| 303.166296 | KSS | AGGV |
| 303.166296 | KSS | ANV |
| 303.166296 | KSS | GGGI |
| 303.166296 | KSS | GGGL |
| 303.166296 | KSS | GIN |
| 303.166296 | KSS | GLN |
| 303.166296 | KSS | GQV |
| 310.139747 | DPP | AGY |
| 310.139747 | DPP | FGS |
| 310.139747 | DPP | QY |
| 314.171047 | AEI | PPT |
| 314.171047 | AEL | PPT |
| 314.171047 | DVV | PPT |
| 317.181946 | KST | AAGV |
| 317.181946 | KST | AGGI |
| 317.181946 | KST | AGGL |
| 317.181946 | KST | AIN |
| 317.181946 | KST | ALN |
| 317.181946 | KST | AQV |
| 317.181946 | KST | GIQ |
| 317.181946 | KST | GLQ |
| 322.187366 | AHI | FR |
| 322.187366 | AHL | FR |
| 324.155397 | EPP | AAY |
| 324.155397 | EPP | AFS |
| 324.155397 | EPP | FGT |
| 338.134662 | SSY | DFG |
| 338.182281 | HIS | RY |
| 338.182281 | HLS | RY |
| 338.182281 | HTV | RY |
| 340.197931 | GGKP | AHI |
| 340.197931 | GGKP | AHL |
| 340.197931 | KNP | AHI |
| 340.197931 | KNP | AHL |
| 341.193180 | PRS | GHK |
| 341.218332 | AAVV | KPP |
| 341.218332 | AGIV | KPP |
| 341.218332 | AGLV | KPP |
| 341.218332 | GGII | KPP |
| 341.218332 | GGIL | KPP |
| 341.218332 | GGLL | KPP |
| 341.218332 | IIN | KPP |
| 341.218332 | ILN | KPP |
| 341.218332 | IQV | KPP |
| 341.218332 | LLN | KPP |
| 341.218332 | LQV | KPP |
| 352.150312 | STY | ADF |
| 352.150312 | STY | EFG |
| 354.213581 | AGKP | HVV |
| 354.213581 | KPQ | HVV |
| 355.208830 | PRT | AHK |
| 356.145226 | EEP | SSY |
| 356.156460 | GGGPS | AEH |
| 356.156460 | GNPS | AEH |
| 368.229231 | AAKP | HIV |
| 368.229231 | AAKP | HLV |
| 369.188094 | DPR | AAAH |
| 369.188094 | DPR | GGHV |
| 369.188094 | DPR | HNV |
| 370.172110 | AGGPS | DHV |
| 370.172110 | ANPS | DHV |
| 370.172110 | GGGPT | DHV |
| 370.172110 | GNPT | DHV |
| 370.172110 | GPQS | DHV |
| 376.186697 | DFI | PPY |
| 376.186697 | DFL | PPY |
| 376.186697 | EFV | PPY |
| 379.197596 | KSY | AAAF |
| 379.197596 | KSY | FGGV |
| 379.197596 | KSY | FNV |
| 379.197596 | PPPS | AAAF |
| 379.197596 | PPPS | FGGV |
| 379.197596 | PPPS | FNV |
| 382.244881 | GKPV | HII |
| 382.244881 | GKPV | HIL |
| 382.244881 | GKPV | HLL |
| 383.203744 | EPR | AGHV |
| 383.203744 | EPR | GGHI |
| 383.203744 | EPR | GGHL |
| 383.203744 | EPR | HIN |
| 383.203744 | EPR | HLN |
| 383.203744 | EPR | HQV |
| 385.255780 | AGKK | IPR |
| 385.255780 | AGKK | LPR |
| 385.255780 | KKQ | IPR |
| 385.255780 | KKQ | LPR |
| 386.185652 | CGKP | HMV |
| 393.213246 | KTY | AFGV |
| 393.213246 | KTY | FGGI |
| 393.213246 | KTY | FGGL |
| 393.213246 | KTY | FIN |
| 393.213246 | KTY | FLN |
| 393.213246 | KTY | FQV |
| 393.213246 | PPPT | AFGV |
| 393.213246 | PPPT | FGGI |
| 393.213246 | PPPT | FGGL |
| 393.213246 | PPPT | FIN |
| 393.213246 | PPPT | FLN |
| 393.213246 | PPPT | FQV |
| 400.201302 | ACKP | HIM |
| 400.201302 | ACKP | HLM |
| 401.214309 | AGGKS | EPR |
| 401.214309 | AKNS | EPR |
| 401.214309 | GGGKT | EPR |
| 401.214309 | GKNT | EPR |
| 401.214309 | GKQS | EPR |
| 402.144181 | CGGPS | DHM |
| 402.144181 | CNPS | DHM |
| 402.213581 | KSW | FHV |
| 412.266679 | AAIR | HKK |
| 412.266679 | AALR | HKK |
| 412.266679 | GRVV | HKK |
| 414.161939 | DGGPS | EEH |
| 414.161939 | DNPS | EEH |
| 416.159831 | ACGPS | EHM |
| 416.159831 | CGGPT | EHM |
| 416.159831 | CNPT | EHM |

TABLE 2-continued

List of amino acid combinations where the b-type ion fragment has the same m/z value (where z = 1) as a y-type ion fragment. This list only includes m/z peaks less than 500. Highlighted items are examples that are consistent with a tryptic peptide. The order of the amino acids is alphabetical to simplify sorting. The pairs are grouped by exact mass. This list only includes those pairs that cannot be derived from a pair with a smaller mass. The remaining 36,131 pairs are all similar to a pair listed below with the addition of an identical amino acid combination mass, such as adding GG to the b-type ion and N to the y-type ion (GG and N have the same mass).

| m/z | b-ion Sequence | y-ion Sequence |
|---|---|---|
| 416.159831 | CPQS | EHM |
| 416.229231 | KTW | FHI |
| 416.229231 | KTW | FHL |
| 418.172110 | GSSW | DFH |
| 428.181612 | TYY | DFF |
| 432.187760 | ASSW | EFH |
| 432.187760 | GGGPY | EFH |
| 432.187760 | GNPY | EFH |
| 432.187760 | GSTW | EFH |
| 441.197990 | DDIP | ASTY |
| 441.197990 | DDIP | FSST |
| 441.197990 | DDIP | GTTY |
| 441.197990 | DDLP | ASTY |
| 441.197990 | DDLP | FSST |
| 441.197990 | DDLP | GTTY |
| 441.197990 | DEPV | ASTY |
| 441.197990 | DEPV | FSST |
| 441.197990 | DEPV | GTTY |
| 446.199387 | DRSS | AAGGGGG |
| 446.199387 | DRSS | AAGGGN |
| 446.199387 | DRSS | AAGNN |
| 446.199387 | DRSS | AGGGGQ |
| 446.199387 | DRSS | AGGNQ |
| 446.199387 | DRSS | ANNQ |
| 446.199387 | DRSS | GGGQQ |
| 446.199387 | DRSS | GNQQ |
| 451.193574 | DHPT | FGGGGG |
| 451.193574 | DHPT | FGGGN |
| 451.193574 | DHPT | FGNN |
| 451.193574 | EHPS | FGGGGG |
| 451.193574 | EHPS | FGGGN |
| 451.193574 | EHPS | FGNN |
| 455.228897 | KYY | AAFF |
| 455.228897 | PPPY | AAFF |
| 460.215037 | DRST | AAAGGGG |
| 460.215037 | DRST | AAAGGN |
| 460.215037 | DRST | AAANN |
| 460.215037 | DRST | AAGGGQ |
| 460.215037 | DRST | AAGNQ |
| 460.215037 | DRST | AGGQQ |
| 460.215037 | DRST | ANQQ |
| 460.215037 | DRST | GGGGGGV |
| 460.215037 | DRST | GGGGNV |
| 460.215037 | DRST | GGNNV |
| 460.215037 | DRST | GQQQ |
| 460.215037 | DRST | NNNV |
| 460.215037 | ERSS | AAAGGGG |
| 460.215037 | ERSS | AAAGGN |
| 460.215037 | ERSS | AAANN |
| 460.215037 | ERSS | AAGGGQ |
| 460.215037 | ERSS | AAGNQ |
| 460.215037 | ERSS | AGGQQ |
| 460.215037 | ERSS | ANQQ |
| 460.215037 | ERSS | GGGGGGV |
| 460.215037 | ERSS | GGGGNV |
| 460.215037 | ERSS | GGNNV |
| 460.215037 | ERSS | GQQQ |
| 460.215037 | ERSS | NNNV |
| 467.188488 | AEEH | GGGGGY |
| 467.188488 | AEEH | GGGNY |
| 467.188488 | AEEH | GNNY |
| 467.188488 | DDHV | GGGGGY |
| 467.188488 | DDHV | GGGNY |
| 467.188488 | DDHV | GNNY |
| 472.324194 | KKKS | AIIR |
| 472.324194 | KKKS | AILR |
| 472.324194 | KKKS | ALLR |
| 472.324194 | KKKS | RVVV |
| 473.170061 | DEMP | CSTY |
| 484.219060 | AEPW | FFGGG |
| 484.219060 | AEPW | FFGN |
| 486.339844 | KKKT | IRVV |
| 486.339844 | KKKT | LRVV |
| 487.241193 | GRSW | HHPP |
| 489.197990 | DEFP | GSYY |
| 498.234710 | DPVW | AFFGG |
| 498.234710 | DPVW | AFFN |
| 498.234710 | DPVW | FFGQ |

TABLE 3

Sequencing via database searching

| | | |
|---|---|---|
| Total number of dta files | 3508 | |
| OMSSA Results | 338 | Number of files for which OMSSA found at least one result |
| CnZion matched with OMSSA alone | 240 | Number of files for which we found the OMSSA result when OMSSA peptides were only options |
| CnZion matched any OMSSA | 232 | Number of files where our technique matched one of the OMSSA results for |
| CnZion matched best OMSSA | 228 | |
| CnZion provided unique solution, which matched best OMSSA | 193 | |

TABLE 4

Comparative mass spectral analysis

| Analysis Type | No. of Spectra | No. Analyzable | Good Result | % Successful Peptide Id. |
|---|---|---|---|---|
| OMSSA | 4847 | 338[a] | 228[a1] | 4.7 |
| c/z ion | 4847 | 1189[b] | 204[b1] | 4.2 |
| OMSSA & c/z ion | 4847 | 1198[b] | 289 | 5.9 |

[a] OMSSA returned a result;
[a1] E < 0.01 result is not random
[b] Greater than 4 valid peaks;
[b1] best matched peptide with >4 concordant peaks

We claim:

1. A method for determining a composition of a polypeptide, said method comprising:
    introducing said polypeptide to a mass spectrometer;
    selectively fragmenting said polypeptide to generate c and z-type product ions;
    providing a database of mass-to-charge values for possible c and z-type product ions from possible amino acid sequences;

distinguishing said z-type product ions from said c-type product ions by measuring the mass-to-charge ratio of said z-type product ions and said c-type product ions at a mass accuracy better than or equal to 20 ppm sufficient to distinguish said z-type product ions from said c-type product ions, comparing the measured mass-to-charge ratio to said database of mass-to-charge values;

assigning chemical compositions to a plurality of c and z-type product ions from said comparing step to obtain a chemical composition vector that describes a combination of amino acids from the N or C-terminus of said polypeptide; and determining said composition of said polypeptide by comparing said chemical composition vector to a polypeptide or protein database.

2. The method of claim 1, wherein said mass spectrometer generates said c and z-type product ions by electron transfer dissociation or electron capture dissociation.

3. The method of claim 1, wherein said database of mass-to-charge values comprises the masses of c-type and z-type product ions from all possible sequences of amino acids less than 2000 Da.

4. The method of claim 3, wherein the step of determining said polypeptide composition comprises de novo analysis or peptide database searching.

5. The method of claim 4 further comprising searching said polypeptide composition against amino acid compositions of peptides in a peptide database to identify putative proteins from which said polypeptide is derived.

6. The method of claim 1 further comprising determining an amino acid sequence of said polypeptide, wherein the amino acid sequence is determined by reverse reading of said z-type fragments or by forward reading of said c-type fragments.

7. The method of claim 6 further comprising assigning a unique chemical composition for all of said c-type or z-type product ion.

8. The method of claim 1, wherein one or more amino acids of the polypeptide are post-translationally modified, wherein the post-translational modification is selected from the group consisting of:
   a. acetylation;
   b. methylation;
   c. oxidation; and
   d. phosphorylation.

9. The method of claim 1, further comprising:
   a. providing a proteomics database; and
   b. searching the database against said chemical composition vector to identify putative peptide sequences or proteins from which said polypeptide is derived.

10. The method of claim 1, wherein the identifying step further comprises:
    a. iteratively labeling unidentified ion products as c- or z-type product ions by comparing the unidentified product ions to one or more identified putative chemical compositions by:
        i. determining a mass difference between unidentified higher mass mass-to-charge peaks compared to identified lower mass product ion mass-to-charge peaks and comparing said mass difference to a database of possible amino acid chemical compositions to identify a missing amino acid sequence, and
        ii. identifying gaps associated with the unidentified or missing product ions by determining the total mass of the polypeptide and comparing the missing product ions against said determined composition; and
    b. filling said gaps by supplying said missing amino acid sequence so as to match the determined chemical composition.

11. The method of claim 1 further comprising reducing spectral noise by:
    a. identifying mass regions where all theoretically possible c and z-type product ions accumulate; and
    b. eliminating as spectral noise those product ions with a mass-to-charge ratio having a mass outside said mass regions, wherein the time required for determining said amino acid composition is reduced by one to three orders of magnitude compared to methods where said spectral noise is not eliminated.

12. The method of claim 1, further comprising real-time adjustment of said mass spectrometer to provide intelligent data acquisition for subsequent fragment analysis by:
    a. determining a putative peptide sequence based on a protein database search on said polypeptide composition;
    b. identifying one or more z-type product ions that are capable of being generated from said putative peptide sequence;
    c. selecting a z-type product ion introduced to said mass spectrometer for subsequent analysis based on matching said selected z-type product ion with at least a portion of said putative peptide sequence.

13. The method of claim 1 further comprising obtaining a mass spectrum of product ions and assessing spectrum data quality by:
    a. determining an allowable peak number, wherein said allowable peak number is the number of identified mass-to-charge product ions having at least one c- or z-type putative chemical composition;
    b. identifying a noise fragment number, wherein said noise fragment number is the number of mass-to-charge product ions having no putative chemical compositions;

wherein said mass spectrum is rejected for further analysis if the spectrum has a noise fragment number that is less than or equal to a user-selected noise fragment number or said mass spectrum is selected for further analysis if the spectrum has an allowable peak number that is greater or equal to three.

14. The method of claim 13, further comprising adjusting an instrument parameter to maximize spectrum data quality, wherein said instrument parameter is selected from the group consisting of:
    a. concentration of product ions;
    b. means for fragmenting said polypeptide
    c. period of fragmentation;
    d. energy of fragmentation;
    e. number of anions used for ETD;
    f. type of mass analysis performed;
    g. selection of product ions for subsequent analysis; and
    h. conditions used to effect ECD.

15. The method of claim 1 further comprising obtaining a mass spectrum of said product ions, and said mass spectrum is rejected for said mass spectrum having two or less unambiguously assigned chemical compositions.

16. The method of claim 1, wherein said polypeptide comprises a mixture of polypeptide species, said method further comprising identifying said plurality of polypeptide species by:
    a. reducing spectral noise by
        i. identifying mass regions where all theoretically possible c and z-product ions accumulate;
        ii. eliminating as spectral noise those fragments outside said spectrum regions;

b. separating remaining peaks into multiple lists of compatible peaks.

17. The method of claim 1, further comprising the steps of calibrating said mass spectrometer by:
   a. identifying one or more fragments having an unambiguously assigned chemical composition; and
   b. using said unambiguously assigned chemical composition as a calibrant to recalibrate said spectrometer.

18. A method of real-time selection of polypeptides to be sequenced, from a sample containing one or more polypeptides; said method comprising:
   a. introducing said sample to a mass spectrometer;
   b. selectively fragmenting one or more polypeptides to generate c and z-type product ions;
   c. measuring the mass-to-charge ratio of at least a portion of said c-type product ions, said z-type product ions, or both and calculating a mass therefrom at a mass accuracy better than or equal to 20 ppm to distinguish z-type product ions from c-type product ions;
   d. providing a database containing c-type ion product masses, z-type ion product masses, or both c-type and z-type ion product masses;
   e. matching one or more of said calculated masses with a c or z-type product ion mass in said database to obtain an unambiguously assigned c or z-type product ion chemical composition and an at least a partial sequence of said polypeptide; and
   f. continuously selecting in real-time a subsequent polypeptide of the sample or generated fragment thereof to be sequenced or to be excluded from sequencing based on said matching step, wherein said subsequent polypeptide or fragment thereof are selected or excluded based on said previously at least partially sequenced peptide.

19. A method for calibrating a mass spectrometer, said method comprising:
   a. introducing a polypeptide to said mass spectrometer;
   b. selectively fragmenting said polypeptide to generate c- and z-type product ions;
   c. measuring the mass-to-charge ratio of said c- and z-type product ions at a mass accuracy better than or equal to 20 ppm to distinguish said z-type product ions from said c-type product ions;
   d. identifying at least one c or z-type fragment having a unique and unambiguous chemical composition by matching the measured mass-to-charge ratio to a database of mass-to-charge values for all possible c and z-type product ions; and
   e. calibrating said mass spectrometer by adjusting an instrument parameter of the mass spectrometer so that calculated mass for the product ion having a unique and unambiguous chemical composition corresponds to the mass of said unique chemical composition.

20. A method for determining a composition of a polypeptide, said method comprising:
   introducing said polypeptide to a mass spectrometer by electron transfer dissociation or electron capture dissociation;
   selectively fragmenting said polypeptide to generate c and z-type product ions;
   providing a database of mass-to-charge values for possible c and z-type product ions from possible amino acid sequences;
   distinguishing said z-type product ions from said c-type product ions by measuring the mass-to-charge ratio of said z-type product ions and said c-type product ions at a mass accuracy better than or equal to 20 ppm sufficient to distinguish said z-type product ions from said c-type product ions,
   comparing the measured mass-to-charge ratio to said database of mass-to-charge values;
   assigning chemical compositions to a plurality of c and z-type product ions from said comparing step to obtain a chemical composition vector that describes a combination of amino acids from the N or C-terminus of said polypeptide; and
   determining said composition of said polypeptide by comparing said chemical composition vector to a polypeptide or protein database.

* * * * *